(12) United States Patent
Ringstrand et al.

(10) Patent No.: US 8,168,084 B2
(45) Date of Patent: May 1, 2012

(54) POLAR NEMATIC COMPOUNDS

(75) Inventors: Bryan Ringstrand, Antioch, TN (US); Piotr Kaszynski, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 12/912,712

(22) Filed: Oct. 26, 2010

(65) Prior Publication Data
US 2011/0147655 A1    Jun. 23, 2011

Related U.S. Application Data

(60) Provisional application No. 61/287,863, filed on Dec. 18, 2009.

(51) Int. Cl.
*C09K 19/00* (2006.01)
*C09K 19/06* (2006.01)
*C09K 19/36* (2006.01)
*C09K 19/52* (2006.01)

(52) U.S. Cl. ........... 252/299.6; 252/299.01; 252/299.61; 430/20; 549/4; 349/1; 349/56; 345/87; 428/1.1

(58) Field of Classification Search . 549/4; 252/299.01, 252/299.6, 299.61; 430/20; 349/1, 56; 345/87; 428/1.1

See application file for complete search history.

(56) References Cited

U.S. PATENT DOCUMENTS

| | | | |
|---|---|---|---|
| 6,664,426 B1 * | 12/2003 | Hawthorne et al. ............... 568/5 |
| 7,258,902 B2 | 8/2007 | Parker et al. |
| 7,294,369 B2 | 11/2007 | Harding et al. |
| 7,318,950 B2 | 1/2008 | Kirsch et al. |
| 7,333,166 B2 | 2/2008 | Stephenson, III et al. |
| 7,372,530 B2 | 5/2008 | Stephenson et al. |
| 7,382,424 B2 | 6/2008 | Chari et al. |
| 7,387,856 B2 | 6/2008 | Chari et al. |
| 7,387,858 B2 | 6/2008 | Chari et al. |
| 7,394,506 B2 | 7/2008 | Cirkel et al. |
| 7,410,825 B2 | 8/2008 | Majumdar et al. |

(Continued)

OTHER PUBLICATIONS

Boller, A. et al., "Synthesis and Some Physical Properties of Phenylpyrimidines," J. Mol. Cry. Liq. Cryst. (1977) 42:215-231.

(Continued)

*Primary Examiner* — Geraldina Visconti
(74) *Attorney, Agent, or Firm* — Michael Best & Friedrich, LLP

(57) ABSTRACT

Polar nematic compounds, one example of which has the following structure:

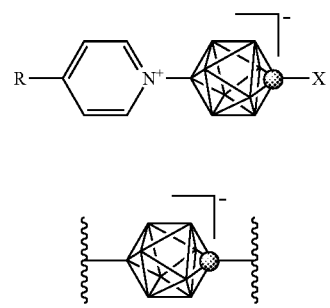

is a caged boron structure, where the sphere of the caged boron structure is C and each non-sphere vertex of the caged boron structure is B—H. R is H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or R is a group that forms an ether, a ketone, an ester, a thioester, a sulfide, or a sulfone. X is COOR' or COSR'. R' is H, an alkyl, a cycloalkyl, a bicycloalkyl, an alkenyl, a cycloalkenyl, a bicycloalkenyl, an alkynyl, an aryl, a halogen, or a cyano group. The compounds may be used in liquid crystal displays (LCDs), and in television sets, laptop computers, computer monitors, hand-held communication devices, gaming devices, watches, cash registers, clocks, and calculators having liquid crystal displays.

12 Claims, 9 Drawing Sheets

U.S. PATENT DOCUMENTS

| | | | |
|---|---|---|---|
| 7,414,313 B2 | 8/2008 | Majumdar et al. |
| 7,416,684 B2 | 8/2008 | Rankin, Jr. et al. |
| 7,425,356 B2 | 9/2008 | Taugerbeck et al. |
| 7,427,441 B2 | 9/2008 | Majumdar et al. |
| 7,438,832 B2 | 10/2008 | Majumdar et al. |
| 7,440,160 B2 | 10/2008 | Heckmeier et al. |
| 7,442,475 B2 | 10/2008 | Farrand et al. |
| 7,445,819 B2 | 11/2008 | Czanta et al. |
| 7,452,482 B2 | 11/2008 | Welter |
| 7,452,575 B2 | 11/2008 | Francis et al. |
| 7,465,479 B2 | 12/2008 | Bremer et al. |
| 7,470,376 B2 | 12/2008 | Welter et al. |
| 7,473,448 B2 | 1/2009 | Shukla et al. |
| 7,482,044 B2 | 1/2009 | Czanta et al. |
| 7,507,449 B2 | 3/2009 | Chari et al. |
| 7,531,106 B2 | 5/2009 | Kirsch et al. |
| 7,532,290 B2 | 5/2009 | Majumdar et al. |
| 7,553,522 B2 | 6/2009 | Heckmeieer et al. |
| 7,557,875 B2 | 7/2009 | Majumdar et al. |
| 7,563,389 B2 | 7/2009 | Shukla et al. |
| 7,563,491 B2 | 7/2009 | Czanta et al. |
| 7,564,528 B2 | 7/2009 | Burberry et al. |
| 7,579,053 B2 | 8/2009 | Czanta et al. |
| 7,583,834 B2 | 9/2009 | McCollough et al. |
| 7,630,029 B2 | 12/2009 | Majumdar et al. |
| 7,638,780 B2 | 12/2009 | Kilburn et al. |
| 7,642,035 B2 | 1/2010 | Shukla et al. |
| 7,645,497 B2 | 1/2010 | Spath et al. |
| 7,675,594 B2 | 3/2010 | Lee et al. |
| 7,682,671 B2 | 3/2010 | Czanta et al. |
| 7,691,455 B2 | 4/2010 | Czanta et al. |
| 7,704,568 B2 | 4/2010 | Shukla et al. |
| 7,710,522 B1 | 5/2010 | Li et al. |
| 7,740,918 B2 | 6/2010 | Czanta et al. |
| 7,754,295 B2 | 7/2010 | Chari et al. |
| 7,771,800 B2 | 8/2010 | Farrand |
| 7,771,801 B2 | 8/2010 | Farrand |
| 7,781,047 B2 | 8/2010 | Majumdar et al. |
| 7,794,621 B2 | 9/2010 | Schott et al. |
| 7,812,919 B2 | 10/2010 | Chien et al. |

OTHER PUBLICATIONS

Brellochs, B.; et al., "New Routes to Carboranes," Contemporary Boron Chemistry (2000) 212-214.

Franken, A.; et al., "Polyhedral Monocarbaborane Chemistry. A Review of Recent Developments Among C-ARYL Monocarbaborane Systems," Collect. of Czech. Chem. Commun. (2002) 67:869-912.

Franken, A.; et al. "Monocarbaborane Anion Chemistry. {COOH}, {CH2OH} and {CHO} Units as Functional Groups on Ten-vertex Monocarbaborane Anionic Compounds," Dalton Trans. (2004) 3552-3561.

Fréedericksz, V. et al., "Forces Causing the Orientation of an Anisotropic Liquid," Trans. Faraday Soc. (1933) 29:919-930.

Gray, G. et al., "The Synthesis and Transition Temperatures of Some Fluoro-Substituted 4-Cyanophenyl and 4-Cyanobiphenyl-4'-yl 4-Pentyl- and 4-Botoxy-Benzoates," Mol. Cryst. Liq. Cryst. (1989) 172:165-189.

Huang, X. et al., "New Ammonia Equivalents for the Pd-Catalyzed Amination of Aryl Halides," Org. Lett. (2001) 3:21:3417-3419.

Klausen, M. et al., "Calculation of Optical and Dielectric Anisotropy of Nematic Liquid Crystals," Jpn. J. Appl. Phys. (1998) 37:L945-L948.

Maier, V. et al., "Eine Einfache Theorie der Dielektrischen Eigenschaften Homogen Orientierter Kristallinflussiger Phasen des Nematischen," Naturforschg. (1961) 16A, 262-267.

McDonnell, D. G. et al., "Dipole Moments and Dielectric Properties of Fluorine Substituted Nematic Liquid Crystals," Liq. Cryst. (1989) 6:3:515-523.

Naemura, S.. "Dielectric Properties of NEmatics for Applications," Physical Properties of Liquid Crystals: Nematics, (2001) 523-581.

Pakhomov, S. et al., "10-Vertex Closo-Boranes as Potential p Linkers for Electronic Materials", Inorg. Chem. (2000) 39: 2243-2245.

Rague Schleyer, P.V. et al., "Stability and Three-Dimensional Aromaticity of Closo-Monocarbaborane Anions, CBn-1Hn-, and Closo-Dicarboranes, C2Bn-2Hn," Inorg. Chem. (1998) 37:3454-3470.

Ringstrand, B. et al., Anion-driven Mesogenicity: Ionic Liquid Crystals Based on the [closo-1-CB9H10]—Cluster, J. Mater. Chem. (2009) 19:4805-4812.

Ringstrand, B. et al., "Polar Drivatives of the [closo-1-CB9H10]—Cluster as Positive Δε Additives to Nematic Hosts," J. Mater. Chem. (2009) 19:9204-9212.

Ringstrand, B. et al., "Synthesis and Reactivity of [closo-1-CB9H9-1-N2]: Functional Group Interconversion at the Carbon Vertex of the {closo-1-CB9} Cluster," Inorg. Chem. (2009) 48:7313-7329.

Ringstrand, B. et al., "Anionic Amino Acid [closo-1-CB9H8-1-COO-10-NH3]- and Dinitrogen Acid [closo-1-CB9H8-1-COOH-10-N2] as Key Precursors to Advanced Materials: Synthesis and Reactivity," Inorg. Chem. (2010) 49:1166-1179.

Ringstrand, B. et al., "How Much Can an Electric Dipole Stabilize a Nematic Phase? Polar and Non-Polar Isosteric Derivatives of [closo-1-CB9H10]- and [closo-1,10-C2B8H10]," J. Mater. Chem. (2010) 20:9613-9615.

Ringstrand, B. et al., High Δε Nematic Liquid Crystals: Fluxional Sqitterions of the [closo-1-CB9H10]—Cluster, J. Mater. Chem. DOI:10.1039/c0jm02075c, (2010) 1-7.

Ringstrand, B. et al., "A Practical Synthesis of Isomerically Pure 1,10-Difunctionalized Derivatives of the [closo-1-CB9H10] Anion," Inorg. Chem., (2005) 44:25:9561-9566.

Ringstrand, B., et al., "How Much Can an Electric Dipole Stabilize a Nematic Phase? Polar and Non-Polar Isosteric Derivatives of [closo-1-CB9H10] and [closo-1,10-C2B8H10]," J. Mater. Chem. (2010) 1-4.

Ringstrand, G. et al., "Anionic Amino Acid [closo-1-CB9H8-1-COO-10-NH3] and Dinitrogen Acid [closo-1-CB9H8-1-COOH-10-N2] as Key Precursors to Advanced Materials: Synthesis and Reactivity," Inorganic Chem. (2009) 1-14.

Takimoto, S. et al., Esterification of Aromatic Carboxylic Acids with Alcohols Using 2-Chloro-3,5-dinitropyridine as a Condensing Agent, Bull. Chem. Soc. Jpn. (1983) 56:639-640.

Urban, S., "Static Dielectric Properties of Nematics," Physical Properties of Liquid Crystals: Nematics, (2001) 267-276.

Yelamaggad, C.V. et al., "Self-Assembly of Chiral Mesoionic Heterocycles into Smectic Phases: a New Clas of Polar Liquid Crystal,"Tetrahedron Lett. (2005) 46:2623-2626.

Wu, S.T. et al., "Physical Properties of Chlorinated Liquid Crystals," Liq. Cryst. (1991) 10:5:635-646.

\* cited by examiner

POLAR NEMATIC COMPOUNDS

CROSS-REFERENCE TO RELATED APPLICATIONS

This patent application claims the benefit of U.S. Provisional Application No. 61/287,863, filed Dec. 18, 2009, the content of which is incorporated herein by reference in its entirety.

STATEMENT REGARDING FEDERALLY SPONSORED RESEARCH

This invention was made with government support under DMR-0606317 and DMR-0907542 awarded by the National Science Foundation. The government has certain rights in the invention.

INTRODUCTION

Nearly all liquid crystal (LC) electrooptical devices, such as flat panel displays, rely on the so-called Freedericksz transition, where polar oriented molecules re-orientate in an external electric field resulting in a change of the optical properties of the bulk material. See, Freedericksz and Zolina, Trans. Faraday Soc., vol. 29, pp. 919-930 (1933), the content of which is herein incorporated by reference in its entirety. The threshold voltage ($V_{th}$) for the reorientation of the LC molecules is inversely proportional to the square root of dielectric anisotropy, $\Delta\epsilon$, which in turn is proportional to the molecular dipole moment and its orientation relative to the main molecular axis, $\sim\mu^2(1-3\cos^2\beta)$. Therefore, the larger the dipole moment, the lower the threshold voltage ($V_{th}\sim 1/\mu$).

Liquid crystals with positive anisotropy of dielectric permittivity ($\Delta\epsilon>0$) are typically designed by using polar terminal substituents, such as —CN, —NCS, and F, or heterocycles, such as pyrimidine or dioxane, as part of the rigid core, with the net dipole moment oriented along the long molecular axis. Dipole moments associated with these molecular fragments are moderate and generally do not exceed 5 Debye (D) (e.g., for benzonitrile $\mu$=4.52 D). Much larger molecular dipole moments are observed for zwitterions, and for some compounds, values near 16 D have been measured. Anisometric compounds (elongated molecular shapes) possessing such large dipole moments could serve as effective low-concentration polar additives that significantly increase $\Delta\epsilon$ of the liquid crystalline material. However, most zwitterions have geometries incompatible with a typical nematic LC material, which limits their usefulness in electrooptical applications. To date only three classes of zwitterionic mesogens, pyrazo[1,2-a]pyrazoliumolates, syndones, and N-pyridinio-4-alkoxybenzamidates, have been reported. New polar nematic compounds, with large molecular dipole moments, may be useful for making products that include liquid crystals.

DETAILED DESCRIPTION

Figure 1:
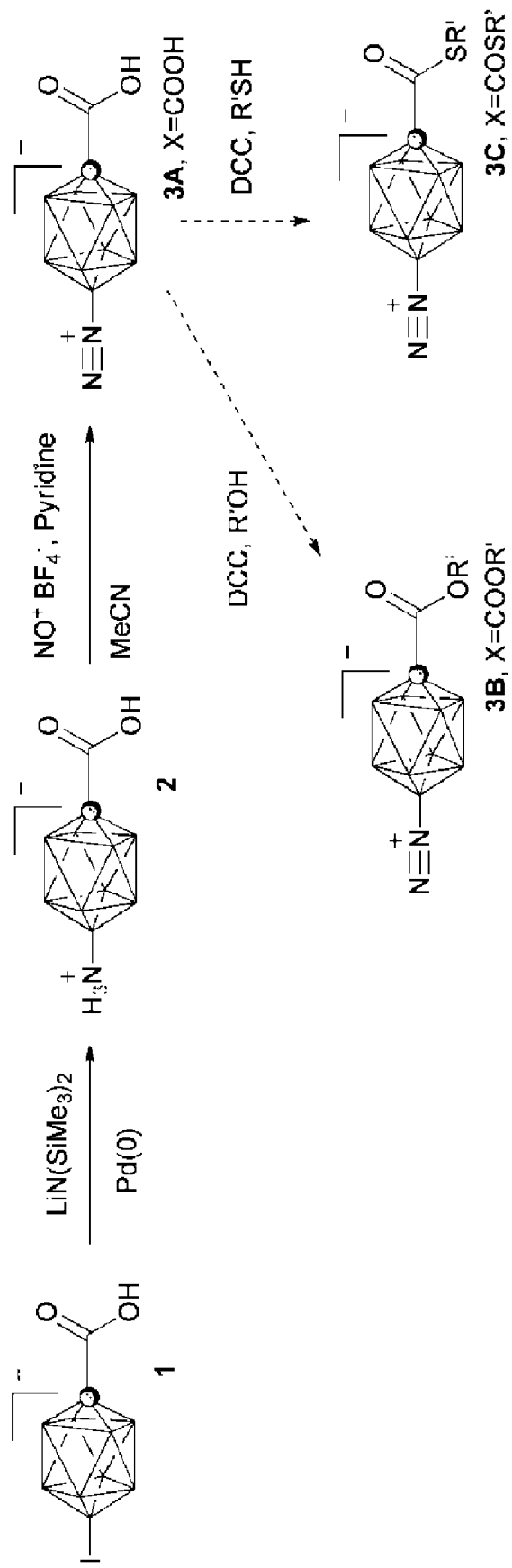
FIG. 1 is a flow chart showing the synthesis of [closo-1-CB$_9$H$_8$-1-COOH-10-N$_2$], [closo-1-CB$_9$H$_8$-1-COOR'-10-N$_2$], and [closo-1-CB$_9$H$_8$-1-COSR'-10-N$_2$] from [closo-1-CB$_9$H$_{10}$-1-COOH-10-I]$^-$.

The present disclosure is not limited in its application to the specific details of construction, arrangement of components, or method steps set forth herein. The compositions and methods disclosed herein are capable of being made, practiced, used, carried out and/or formed in various ways. The phraseology and terminology used herein is for the purpose of description only and should not be regarded as limiting. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification, and no structures shown in the drawings, should be construed as indicating that any non-claimed element is essential to the practice of the invention. The use herein of the terms "including," "comprising," or "having," and variations thereof, is meant to encompass the items listed thereafter and equivalents thereof, as well as additional items. Unless specified or limited otherwise, the terms "mounted," "connected," "supported," and "coupled" and variations thereof encompass both direct and indirect mountings, connections, supports, and couplings. Further, "connected" and "coupled" are not restricted to physical or mechanical connections or couplings.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein. All references cited herein are fully incorporated by reference, unless explicitly indicated otherwise. The present disclosure shall control in the event there are any disparities.

The following definitions shall apply unless otherwise indicated.

The term "acyl," as used herein, refers to a group having the general structure —C(═O)R, wherein R is an acyl substituent including, but not limited to, H, an alkyl, an alkenyl, an alkynyl, a cyclic alkyl, a cyclic alkenyl, and an aryl, among others. Suitable examples of acyl groups include, but are not limited to, —C(═O)CH$_3$ (acetyl), —C(═O)CH$_2$CH$_3$ (propionyl), —C(═O)CH$_2$CH$_2$CH$_3$ (butyryl), and —C(═O)Ph (benzoyl, phenone).

The term "alkenyl," as used herein, refers to an unsaturated hydrocarbon chain having at least one double bond 2 to 12 carbon atoms. Suitable examples include alkenyls having 2 to 7 carbon atoms, 2 to 6 carbon atoms, 2 to 5 carbon atoms, 2 to 4 carbon atoms or 2 to 3 carbon atoms. Alkenyl groups may have more than one double bond. Alkenyl groups also may have one or more triple bonds. For example, alkenyl groups may have one or more double bonds and one or more triple bonds. Alkenyl groups may be straight or branched, and branched alkenyl groups may have one or more branches. Alkenyl groups may be unsubstituted or may have one or more independent substituents, unless otherwise specified. Each substituent may include, but is not limited to, an alkyl, a cycloalkyl, a bicycloalkyl, an alkenyl, a cycloalkenyl, a bicycloalkenyl, an alkynyl, an acyl, an aryl, a cyano group, a halogen, a hydroxyl group, a carboxyl group, an isothiocyanoto group, an ether, an ester, a ketone, a sulfoxide, a sulfone, a thioether, a thioester, a thiol group, an amino, an amido, or a nitro group, among others. Each substituent also may include any group that, in conjunction with the alkenyl, forms an ether, an ester, a ketone, a thioether, a thioester, a sulfoxide, a sulfone, an amine or an amide, among others. Some alkenyl groups may have one or more chiral carbons because of the branching or substitution. Chiral alkenyl groups include both (+)dextrorotary and (−)levorotary compounds; "D-" and "L-" chiral compounds, as well as alkenyl groups containing "R-" and "S-" stereocenters. Some alkenyl groups may include one or more heteroatoms.

The terms "alkoxy," or "alkoxyl," as used herein, refer to functional groups or substituents having the general structure —OR, where R is an alkoxy substituent. R is not limited to an alkyl and may include an alkyl, an alkenyl, an alkynyl, a cycloalkyl, a cycloalkynyl, and an aryl, among others.

The term "alkyl," as used herein, refers to a saturated hydrocarbon chain having 1 to 12 carbon atoms. Suitable examples include alkyls having 1 to 7 carbon atoms, 1 to 6 carbon atoms, 1 to 5 carbon atoms, 1 to 4 carbon atoms or 1 to 3 carbon atoms. Alkyl groups may be straight or branched, and branched alkyl groups may have one or more branches. Alkyl groups may be unsubstituted or may have one or more independent substituents, unless otherwise specified. Each substituent may include, but is not limited to an alkyl, a cycloalkyl, a bicycloalkyl, an alkenyl, a cycloalkenyl, a bicycloalkenyl, an alkynyl, an acyl, an aryl, a cyano group, a halogen, a hydroxyl group, a carboxyl group, an isothiocyanoto group, an ether, an ester, a ketone, a sulfoxide, a sulfone, a thioether, a thioester, a thiol group, an amino, an amido, or a nitro group, among others. Each substituent also may include any group that, in conjunction with the alkyl, forms an ether, an ester, a ketone, a thioether, a thioester, a sulfoxide, a sulfone, an amine or an amide, among others. Some alkyl groups may have one or more chiral carbons because of the branching or substitution. Chiral alkyl groups include both (+)dextrorotary and (−)levorotary compounds; "D-" and "L-" chiral compounds, as well as alkyl groups containing "R-" and "S-" stereocenters. Some alkyl groups may include one or more heteroatoms.

The term "alkynyl," as used herein, refers to an unsaturated hydrocarbon chain having at least one triple bond and 2 to 12 carbon atoms. Suitable examples include alkynyls having 2 to 7 carbon atoms, 2 to 6 carbon atoms, 2 to 5 carbon atoms, 2 to 4 carbon atoms or 2 to 3 carbon atoms. Alkynyl groups may have more than one triple bond. Alkynyl groups also may have one or more double bonds. For example, alkynyl groups may have one or more double bonds and one or more triple bonds. Alkynyl groups may be straight or branched, and branched alkynyl groups may have one or more branches. Alkynyl groups may be unsubstituted or may have one or more independent substituents, unless otherwise specified. Each substituent may include, but is not limited to an alkyl, a cycloalkyl, a bicycloalkyl, an alkenyl, a cycloalkenyl, a bicycloalkenyl, an alkynyl, an acyl, an aryl, a cyano group, a halogen, a hydroxyl group, a carboxyl group, an isothiocyanoto group, an ether, an ester, a ketone, a sulfoxide, a sulfone, a thioether, a thioester, a thiol group, an amino, an amido, or a nitro group, among others. Each substituent also may include any group that, in conjunction with the alkynyl, forms an ether, an ester, a ketone, a thioether, a thioester, a sulfoxide, a sulfone, an amine or an amide, among others. Some alkynyl groups may have one or more chiral carbons because of the branching or substitution. Chiral alkynyl groups include both (+)dextrorotary and (−)levorotary compounds; "D-" and "L-" chiral compounds, as well as alkynyl groups containing "R-" and "S-" stereocenters. Some alkynyl groups may include one or more heteroatoms.

The term "alkyaryl," as used herein, refers to an alkyl group having one or more aryl substituents.

The term "aryl," as used herein, refers to any functional group or substituent group derived from an aromatic hydrocarbon ring system. Aromatic rings may be monocyclic or fused multicyclic ring systems. Monocyclic aromatic rings contain from about 4 to about 10 carbon atoms, such as from 5 to 7 carbon atoms, or from 5 to 6 carbon atoms in the ring.

Multicyclic aromatic rings may contain from about 4 to about 10 carbon atoms per ring, and from 2 to about 4 rings, where adjacent rings may share two or more carbon atoms. Aromatic rings may be unsubstituted or may have one or more independent substituents on the ring. Each substituent may include, but is not limited to an alkyl, a cycloalkyl, a bicycloalkyl, an alkenyl, a cycloalkenyl, a bicycloalkenyl, an alkynyl, an acyl, an aryl, a cyano group, a halogen, a hydroxyl group, a carboxyl group, an isothiocyanoto group, an ether, an ester, a ketone, a sulfoxide, a sulfone, a thioether, a thioester, a thiol group, an amino, an amido, or a nitro group, among others. Each substituent also may include any group that, in conjunction with the aryl, forms an ether, an ester, a ketone, a thioether, a thioester, a sulfoxide, a sulfone, an amine or an amide, among others. Some aryl groups may include one or more heteroatoms.

The term "amide," as used herein, refers to a group having the general structure $RC(=O)NR^1R^2$, wherein N, $R^1$ and $R^2$ are an amido group and R which is an independent substituent that may include an alkyl, an alkenyl, an alkynyl, a cycloalkyl, a cycloalkenyl, and an aryl among others.

The term "amido," as used herein, refers to a group having the general structure $—C(=O)NR^1R^2$, wherein $R^1$ and $R^2$ are independently amino substituents, as defined for amino groups. Examples of amido groups include, but are not limited to, $—C(=O)NH_2$, $—C(=O)NHCH_3$, $—C(=O)N(CH_3)_2$, $—C(=O)NHCH_2CH_3$, and $—C(=O)N(CH_2CH_3)_2$. as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl. Cyclic amido groups may be substituted on their ring by other substituents and/or may include one or more other heteroatoms.

The term "amine," as used herein, refers to a group having the general structure $NR^1R^2R^3$, wherein N, $R^1$ and $R^2$ are an amino group attached to $R^3$, which is an independent substituent.

The term "amino," as used herein, refers to a group having the general structure $—NR^1R^2$, wherein $R^1$ and $R^2$ are independently amino substituents including, but not limited to, hydrogen, an alkyl, an alkenyl, an alkynyl, a cycloalkyl, a cycloalkenyl, or an aryl group, among others or, in the case of a "cyclic" amino group, $R^1$ and $R^2$, taken together with the nitrogen atom to which they are attached form a heterocyclic ring having from 3 to 8 ring atoms. Examples of amino groups include, but are not limited to, $—NH_2$, $—NHCH_3$, $—NHCH(CH_3)_2$, $—N(CH_3)_2$, $—N(CH_2CH_3)_2$, $—NHPh$, etc. Examples of cyclic amino groups include, but are not limited to, aziridinyl, azetidinyl, pyrrolidinyl, piperidino, piperazinyl, perhydrodiazepinyl, morpholino, and thiomorpholino. Cyclic amino groups also may be substituted on their ring by other substituents, and/or may include one or more other heteroatoms.

The term "carboxyl," as used herein, refers to the group —COOH.

The term "cycloalkenyl," as used herein, refers to any functional group or substituent having an unsaturated hydrocarbon ring that is non-aromatic. Cycloalkenyls have one or more double bonds. Cycloalkenyls are monocyclic, or are fused, spiro, or bridged bicyclic ring systems, where the term "bicycloalkenyl," as used herein, refers to such bicyclic unsaturated ring structures. Monocyclic cycloalkenyls contain from about 3 to about 10 carbon atoms, such as from 4 to 7 carbon atoms, or from 5 to 6 carbon atoms in the ring. Bicycloalkenyls contain from 5 to 12 carbon atoms, such as from 8 to 10 carbon atoms in the ring. Cycloalkenyls may be unsubstituted or may have one or more independent substituents on the ring. Each substituent may include, but is not limited to an alkyl, a cycloalkyl, a bicycloalkyl, an alkenyl, a cycloalkenyl, a bicycloalkenyl, an alkynyl, an acyl, an aryl, a cyano group, a halogen, a hydroxyl group, a carboxyl group, an isothiocyanoto group, an ether, an ester, a ketone, a sulfoxide, a sulfone, a thioether, a thioester, a thiol group, an amino, an amido, or a nitro group, among others. Each substituent also may include any group that, in conjunction with the cycloalkenyl, forms an ether, an ester, a ketone, a thioether, a thioester, a sulfoxide, a sulfone, an amine or an amide, among others. Cycloalkenyl groups may have one or more chiral carbons because of the substitution. Some cycloalkenyl groups may include one or more heteroatoms. Examples of cycloalkenyls include, but are not limited to cyclopropenyl, cyclohexenyl, 1,4 cyclooctadienyl, and bicyclooctenyl, among numerous others.

The term "cycloalkyl," as used herein, refers to any functional group or substituent having a saturated hydrocarbon ring that is non-aromatic. Cycloalkyls are monocyclic, or are fused, spiro, or bridged bicyclic saturated ring systems, where the term "bicycloalkyl," as used herein, refers to such bicyclic saturated ring structures. Monocyclic cycloalkyls contain from about 3 to about 10 carbon atoms, such as from 4 to 7 carbon atoms, or from 5 to 6 carbon atoms in the ring. Bicycloalkyls contain from 5 to 12 carbon atoms, such as from 8 to 10 carbon atoms in the ring. Cycloalkyls may be unsubstituted or may have one or more independent substituents on the ring. Each substituent may include, but is not limited to an alkyl, a cycloalkyl, a bicycloalkyl, an alkenyl, a cycloalkenyl, a bicycloalkenyl, an alkynyl, an acyl, an aryl, a cyano group, a halogen, a hydroxyl group, a carboxyl group, an isothiocyanoto group, an ether, an ester, a ketone, a sulfoxide, a sulfone, a thioether, a thioester, a thiol group, an amino, an amido, or a nitro group, among others. Each substituent also may include any group that, in conjunction with the cycloalkyl, forms an ether, an ester, a ketone, a thioether, a thioester, a sulfoxide, a sulfone, an amine or an amide, among others. Cycloalkyl groups may have one or more chiral carbons because of the substitution. Some cycloalkyl groups may include one or more heteroatoms. Examples of cycloalkyls include, but are not limited to cyclopentyl, cyclohexyl, cycloheptyl, cyclooctyl, bicyclooctyl, and tetrahydropyran, among numerous others.

The term "cyano," as used herein, refers to the group —CN.

The term "diazonium," as used herein, refers to the group $—N_2^+$.

The term "ether," as used herein, refers to the group ROR', where R and R' are ether substituents. R and R' each may include an alkyl, an alkenyl, an alkynyl, a cycloalkyl, a cycloalkynyl, and an aryl, among others.

The term "ester," as used herein, refers to the group $RC(=O)OR'$, wherein R and R' are ester substituents. R and R' each may include an alkyl, an alkenyl, an alkynyl, a cycloalkyl, a cycloalkynyl, and an aryl, among others.

The term "halogen," as used herein, refers to fluorine, chlorine, bromine or iodine. Halogens are not heteroatoms.

The term "heteroatom," as used herein, refers to a nitrogen, sulfur, or oxygen atom. Groups containing more than one heteroatom may contain different heteroatoms.

The term "hydroxyl," as used herein, refers to the group —OH.

The term "isothiocyanoto," as used herein, refers to the group: —SCN.

The term "ketone," as used herein, refers to the group $RC(=O)R'$, wherein R and R' are ketone substituents. R and R' each may include an H, an alkyl, an alkenyl, an alkynyl, a cycloalkyl, a cycloalkenyl, and an aryl, among others.

The term "nitro," as used herein, refers to the group —$NO_2$.

The term "pyridinium," as used herein, refers to the cationic form of pyridine.

The term "saturated," as used herein, means that a moiety has no units of unsaturation.

The term "sulfoxide," as used herein, refers to the group RS(=O)R', wherein R and R' are sulfoxide substituents. R and R' each may include an alkyl, and alkenyl, an alkynyl, a cycloalkyl, a cycloalkenyl, and an aryl, among others.

The term "sulfone," as used herein, refers to the group RS(=O)$_2$R', wherein R and R' are sulfone substituents. R and R' each may include an alkyl, and alkenyl, an alkynyl, a cycloalkyl, a cycloalkenyl, and an aryl, among others.

The terms "sulfonium" and "sulfonium ether," as used herein, refer to the group having the general structure ($S^+$)$R^1R^2R^3$, wherein S, $R^1$ and $R^2$ are a thioether attached to $R^3$, which is an independent substituent. $R^1$ and $R^2$, taken together with the positively charged sulfur atom to which they are attached, may form a heterocyclic ring having from 3 to 8 ring atoms.

The term "thiol," as used herein, refers to the group —SH.

The term "thioether," as used herein, refers to the group RSR', where R and R' are thioether substituents. R and R' each may include an alkyl, an alkenyl, an alkynyl, a cycloalkyl, a cycloalkynyl, and an aryl, among others.

The term "thioester," as used herein, refers to the group RC(=O)SR', wherein R and R' are thioester substituents. R and R' each may include an alkyl, an alkenyl, an alkynyl, a cycloalkyl, a cycloalkynyl, and an aryl, among others.

The term "unsaturated," as used herein, means that a moiety has one or more double or triple bonds.

Closo-carbaborates are becoming increasingly important building blocks for advanced materials such as ionic liquids, lithium ion battery electrolytes, ionic liquid crystals, polar liquid crystals, nonlinear optical materials, and agents for Boron Neutron Capture Therapy and Photodynamic Therapy. The attractiveness of these clusters stems from their electronic features which are manifested in complete charge delocalization, low nucleophilicity, and chemical stability under ambient conditions because of sigma-aromaticity of the skeleton. See, Pakhomov et al., *Inorg. Chem.*, 2000, 39, 2243-2245 and references therein, the entire disclosures of which are herein incorporated by reference in their entireties.

The [closo-1-CB$_9$H$_{10}$]$^-$ cluster may be used as a structural building block for ionic liquid crystals and positive Δ∈ additives to nematic materials. A graphical representation of the caged boron structure of the [closo-1-CB$_9$H$_{10}$]$^-$ cluster is shown below, where the sphere of the caged boron structure is a carbon atom and each non-sphere vertex of the caged boron structure is B—H:

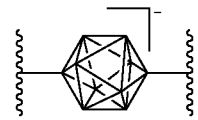

The [closo-1-CB$_9$H$_{10}$]$^-$ cluster may be prepared by the Brellochs method. See, Brellochs, "New Routes to Carboranes," *Contemporary Boron Chemistry*; Davidson, M. G., Hughes, A. K., Marder, T. B., Wade, K., Eds.; Royal Society of Chemistry; Cambridge, England, 2000, pp. 212-214, the complete disclosure of which is herein incorporated by reference in its entirety. As discussed in more detail below, isomerically pure 1,10-difunctionalized derivatives of the [closo-1-CB$_9$H$_{10}$]$^-$ may be prepared by the method disclosed in Ringstrand, B, et al., *Inorg. Chem.,* 2005, 44, 9561-9566, the complete disclosure of which is herein incorporated by reference in its entirety. These 1,10-difunctionalized derivatives may be used to prepare zwitterions substituted in the antipodal positions according to methods disclosed herein.

The present disclosure also provides zwitterions of the [closo-1-CB$_9$H$_{10}$]$^-$ cluster that may be useful as polar mesogens or additives to nematic materials. Substitution of the [closo-1-CB$_9$H$_{10}$]$^-$ cluster with an onium fragment, such as ammonium, diazonium, sulfonium, or pyridinium (among others) gives rise to zwitterions, such as the C1 and B10 bisubstituted zwitterions shown in Classes I-III below:

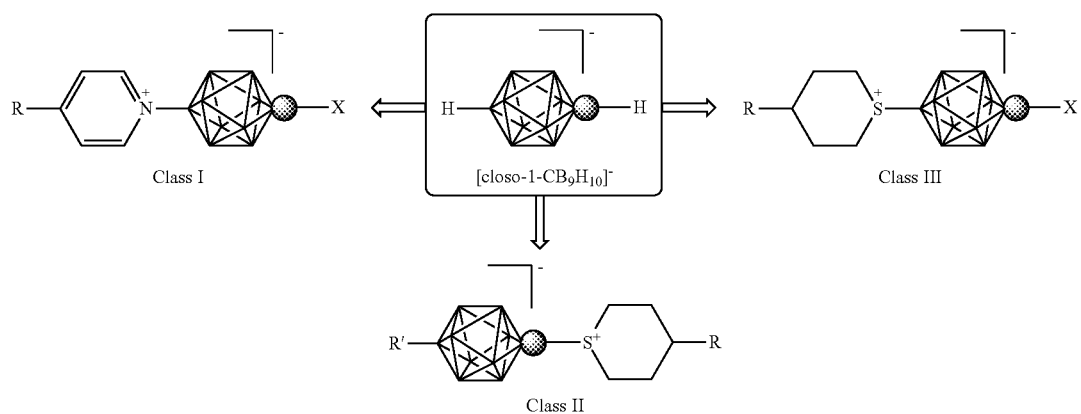

These zwitterions are electrically neutral compounds that may be characterized by a large dipole moment greater than about 8 Debye. Zwitterions substituted in the antipodal positions (i.e., R' and X≠H) have extended molecular shapes (i.e., high aspect ratio) which may be conducive to the formation of liquid crystalline phases and may make these compounds compatible for use in nematic mixtures for liquid crystal displays (LCDs).

I. Class I Compounds—The Zwitterions [closo-1-CB$_9$H$_8$-1-X-10-(1-(4-R—C$_5$H$_4$N))]

The present disclosure provides, among other things, 1,10-disubstituted derivatives of the [closo-1-CB$_9$H$_{10}$]$^-$ cluster having the following structure:

Class I Compounds

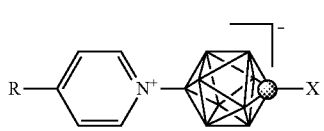

where R may be H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or where R may be a group that, in conjunction with the compound to which it is attached (i.e., the pyridinium ring), forms an ether, a ketone, an ester, a thioester, a sulfide, or a sulfone; where X may be COOH, COOR' or COSR'; and where R' may be H, an alkyl, a cycloalkyl, a bicycloalkyl, an alkenyl, a cycloalkenyl, a bicycloalkenyl, an alkynyl, an aryl, a halogen, or a cyano group. Examples of suitable R substituents for Class I compounds include, but are not limited to, H, a $C_2$-$C_9$ alkyl (e.g., propyl, heptyl, etc.), a $C_2$-$C_9$ alkenyl (e.g., butenyl, henxenyl, etc.), and a $C_2$-$C_9$ alkoxy (e.g., propyloxy, pentyloxy, hexyloxy, heptyloxy, etc.), among others. Examples of suitable R' substituents for Class I compounds include, but are not limited to, a $C_2$-$C_9$ alkyl (e.g., a propyl, a pentyl, a heptyl, a 2-ethylbutyl, etc.), a $C_2$-$C_9$ alkenyl (e.g., a propenyl, a pentenyl, a heptenyl, a 2-ethyl-3-butenyl, etc.), a $C_6$-$C_8$ cycloalkyl (e.g., a substituted or unsubstituted cyclohexyl, a substituted or unsubstituted bicycle[2.2.2]octyl, etc.), and a substituted or unsubstituted aryl (e.g., a phenyl, an alkyl phenyl, an alkenyl phenyl, an alkoxy phenyl, a halogen substituted phenyl, etc.), such as the following compounds, among others:

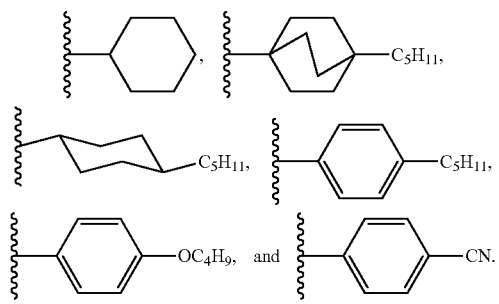

Class I compounds may have a longitudinal component of the molecular dipole moment exceeding about 12 Debye. This large longitudinal component of the molecular dipole moment originates from the zwitterionic structure (i.e., the separated positive and negative charges) of the Class I compounds. These compounds generally may have a melting point that is above ambient temperatures. Specific properties of these compounds, such as melting temperatures, formation of liquid crystalline phases, phase range, and also miscibility with other liquid crystals or nematic hosts, depend on the specific identity of the substituents R and R', as discussed in the Examples.

Figure 2:
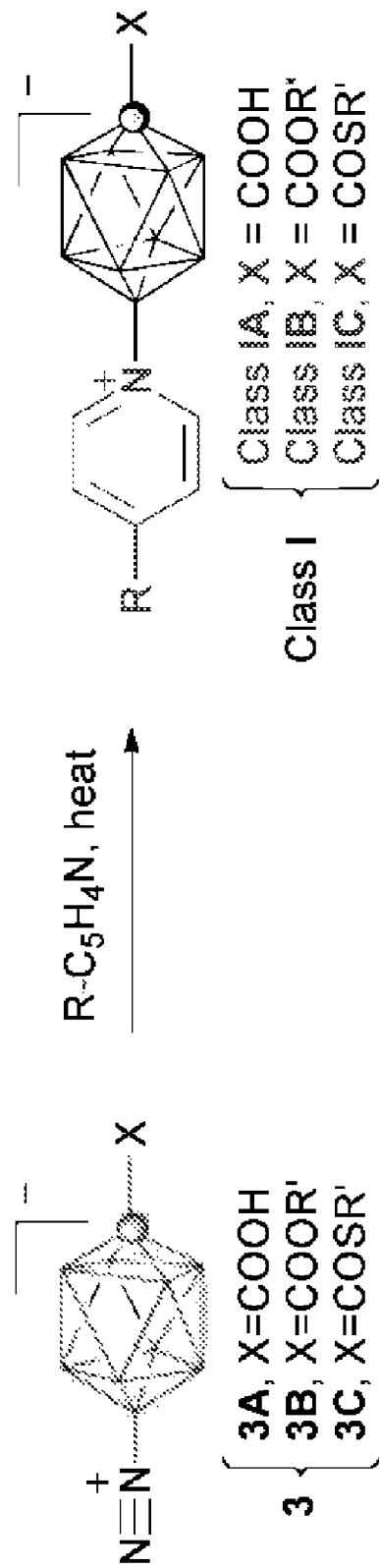
FIG. 2 is a flow chart showing the synthesis of [closo-1-CB$_9$H$_8$-1-COOH-10-(1-(4-R—C$_5$H$_4$N))], [closo-1-CB$_9$H$_8$-1-COOR'-10-(1-(4-R—C$_5$H$_4$N))], and [closo-1-CB$_9$H$_8$-1-COSR'-10-(1-(4-R—C$_5$H$_4$N))] from [closo-1-CB$_9$H$_8$-1-COOH-10-N$_2$], [closo-1-CB$_9$H$_8$-1-COOR'-10-N$_2$], and [closo-1-CB$_9$H$_8$-1-COSR'-10-N$_2$], respectively.
Figure 3:
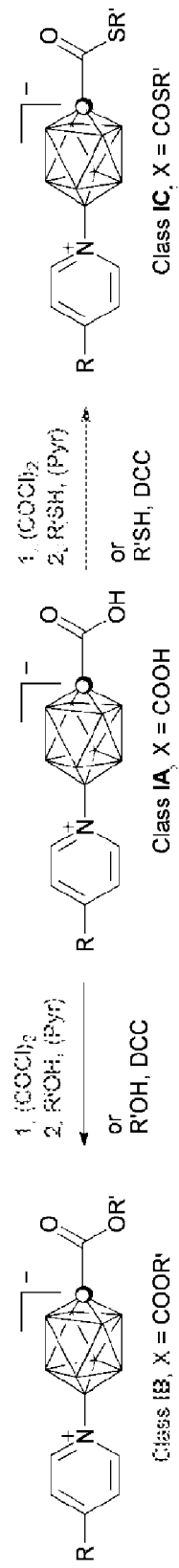
FIG. 3 is a flow chart showing the synthesis of [closo-1-CB$_9$H$_8$-1-COOR'-10-(1-(4-R—C$_5$H$_4$N))] and [closo-1-CB$_9$H$_8$-1-COSR'-10-(1-(4-R—C$_5$H$_4$N))] from [closo-1-CB$_9$H$_8$-1-COOH-10-(1-(4-R—C$_5$H$_4$N))].

FIGS. 1-3 are flow charts showing the general synthesis of Class I compounds. Specifically, they show the various methods of making Class I compounds from [closo-1-$CB_9H_8$-1-COOH-10-I]$^-$ (compound 1). Methods of making compound 1 are disclosed in Ringstrand, B, et al., *Inorg. Chem.*, 2005, 44, 9561-9566, the complete disclosure of which is herein incorporated by reference in its entirety.

As shown in FIG. 1, compound 1 may be reacted with LiN(SiMe$_3$)$_2$ in the presence of a Pd(0) catalyst to form [closo-1-$CB_9H_8$-1-COOH-10-NH$_3$] (compound 2). The compound [closo-1-$CB_9H_8$-1-COOH-10-N$_2$] (compound 3A) then may be synthesized by diazotization of compound 2 with nitrosonium tetrafluoroborate or hexafluorophosphate in the presence of pyridine. The compounds [closo-1-$CB_9H_8$-1-COOR'-10-N$_2$], and [closo-1-$CB_9H_8$-1-COSR'-10-N$_2$] (compounds 3B and 3C, respectively) then optionally may be synthesized by performing an esterification reaction or a thioesterification reaction on compound 3A. For example, esterification of compound 3A with alcohol or phenol R'OH (or thioesterification of compound 3A with mercapto analogues R'SH) under typical esterification conditions causes the formation of compounds 3B and 3C, respectively. For compounds 3B and 3C, R' may be H, an alkyl, a cycloalkyl, a bicycloalkyl, an alkenyl, a cycloalkenyl, a bicycloalkenyl, an alkynyl or an aryl. Compounds 3A, 3B and 3C hereinafter may collectively be referred to as [closo-1-$CB_9H_8$-1-X-10-N$_2$], where X is COOH, COOR' or COSR', or in the alternative as "compound 3." As discussed below, compound 3 may be used as a key intermediate toward the formation of Class I and Class II compounds.

As shown in FIG. 2, Class I compounds may be synthesized by heating a mixture comprising a selected compound 3 (i.e., [closo-1-$CB_9H_8$-1-X-10-N$_2$]) and a desired pyridine derivative (e.g., 4-R—$C_5H_4N$) at, for example, a temperature of about 100° C., although the reaction may be heated at any suitable temperature for a suitable period of time. In this process, the pyridine derivative replaces the diazonium moiety of compound 3 to form the Class I compound [closo-1-$CB_9H_8$-1-X-10-(1-(4-R—$C_5H_4N$))]. For example, if compound 3 is compound 3A (X=COOH), 3B (X=COOR'), or 3C (X=COSR'), then the thermolysis reaction with the pyridine derivative (4-R—$C_5H_4N$) will form a Class IA compound [closo-1-$CB_9H_8$-1-COOH-10-(1-(4-R—$C_5H_4N$))], a Class IB compound [closo-1-$CB_9H_8$-1-COOR'-10-(1-(4-R—$C_5H_4N$))], or a Class IC compound [closo-1-$CB_9H_8$-1-COSR'-10-(1-(4-R—$C_5H_4N$))], respectively. It should be appreciated that the Class IA, IB and IC compounds collectively are referred to herein as [closo-1-$CB_9H_8$-1-X-10-(1-(4-R—$C_5H_4N$))], where X is COOH, COOR' or COSR', or in the alternative as "Class I compounds."

As shown in FIG. 3, if the thermolysis reaction of FIG. 2 is used to form the Class IA compound, then that compound may subsequently be esterified or thioesterified with alcohol or phenol R'OH or their mercapto analogues R'SH under typical conditions to form the Class IB and IC compounds, respectively.

Examples of Class I compounds include, but are not limited to:

(compound IB-a)

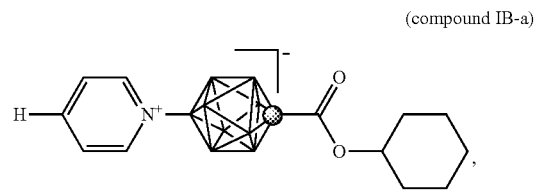

-continued

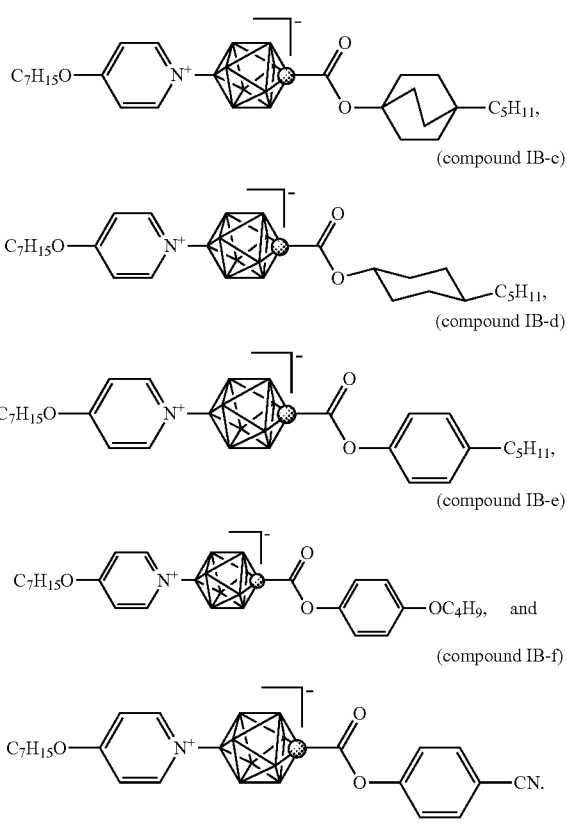

II. Class II Compounds—The Zwitterions [closo-1-CB$_9$H$_8$-1-X-10-(1-(4-R—C$_5$H$_9$S))]

The present disclosure provides, among other things, 1,10-disubstituted derivatives of the [closo-1-CB$_9$H$_{10}$]$^-$ cluster having the following structure:

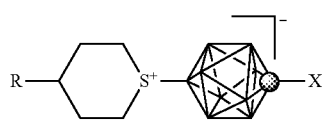

Class II Compounds where R may be H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or where R may be a group that, in conjunction with the compound to which it is attached (i.e., the sulfonium ring), forms an ether, a ketone, an ester, a thioester, a sulfide, or a sulfone; where X may be COOH, COOR' or COSR'; and where R' may be H, an alkyl, a cycloalkyl, a bicycloalkyl, an alkenyl, a cycloalkenyl, a bicycloalkenyl, an alkynyl, or an aryl. Examples of suitable R substituents for Class II compounds include, but are not limited to, a C$_2$-C$_9$ alkyl (e.g., propyl, heptyl, etc.), a C$_2$-C$_9$ alkenyl (e.g., butenyl, henxenyl, etc.), and a C$_2$-C$_9$ alkoxy (e.g., propyloxy, pentyloxy, hexyloxy, heptyloxy, etc.), among others. Examples of suitable R' substituents for Class II compounds include, but are not limited to a C$_2$-C$_9$ alkyl (e.g., a propyl, a pentyl, a heptyl, a 2-ethylbutyl, etc.), a C$_2$-C$_9$ alkenyl (e.g., a propenyl, a pentenyl, a heptenyl, a 2-ethyl-3-butenyl, etc.), a C$_6$-C$_8$ cycloalkyl (e.g., a substituted or unsubstituted cyclohexyl, a substituted or unsubstituted bicyclic[2.2.2]octyl, etc.), and a substituted or unsubstituted aryl (e.g., a phenyl, an alkyl phenyl, an alkenyl phenyl, an alkoxy phenyl, a halogen substituted phenol, etc.), such as the following compounds, among others:

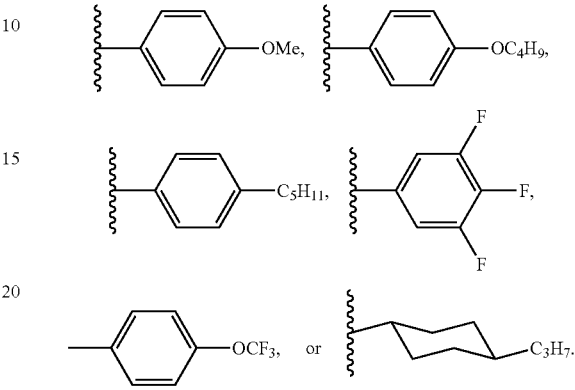

Class II compounds may have a longitudinal component of the molecular dipole moment exceeding about 8 Debye. Like the Class I compounds, the large longitudinal component of the molecular dipole moment for the Class II compounds originates from the zwitterionic structure (i.e., the separated positive and negative charges in the molecule). Also like the Class I compounds, the Class II compounds generally may have a melting point that is above ambient temperatures. However, the Class II compounds may be more soluble in nematic hosts than the Class I compounds, as discussed below. Specific properties of these compounds, such as melting temperatures, formation of liquid crystalline phases, phase range, and also miscibility with other liquid crystals or nematic hosts, depend on the specific identity of the substituents R and R', as discussed in the Examples.

In comparison to Class I compounds, Class II compounds having the same or similar R and R' substituents may form nematic mixtures having lower $\Delta \in$, but also may be more soluble in nematic hosts and may form nematic mixtures having only modestly increased rotational viscosity. These difference may be due to the less anisometric molecular shape of the cyclic sulfonium ester substituent of the Class II compounds. The dynamic anisometry of the Class II compounds may be affected by the fast epimerization at the sulfur center of the cyclic sulfonium substituent of the [closo-1-CB$_9$H$_{10}$]$^-$ cluster between the -trans and -cis epimers (shown below), and the relative orientation of terminal R chains, such as alkyl, alkenyl and alkynyl chains, among others.

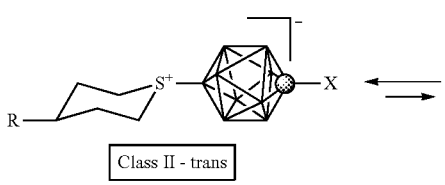

Class II - trans

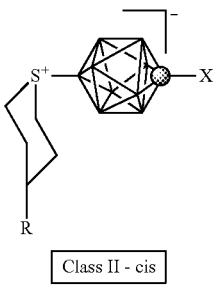

Class II - cis

FIGS. 1 and 4-6 are flow charts showing the general synthesis of Class II compounds. Specifically, they show the various methods of making Class II compounds from [closo-1-CB$_9$H$_{10}$-1-COOH-10-I]$^-$ (compound 1).

As discussed above, FIG. 1 shows methods of making compounds 3A, 3B and 3C, which collectively may be referred to as compound 3. In addition to being useful as a key intermediate for the formation of Class I compounds, compound 3 also may be used as a key intermediate toward the formation of Class II compounds.

Figure 4:
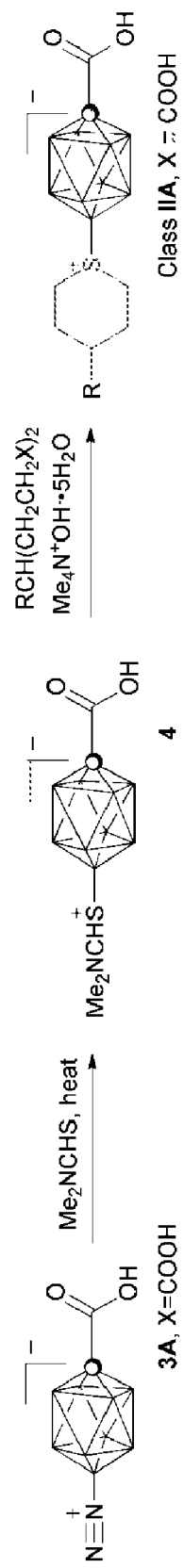
FIG. 4 is a flow chart showing the synthesis of [closo-1-CB$_9$H$_8$-1-COOH-10-(1-(4-R—C$_5$H$_9$S))] from [closo-1-CB$_9$H$_8$-1-COOH-10-N$_2$].

As shown in FIG. 4, compound 3A may be used to form [closo-1-CB$_9$H$_8$-1-COOH-10-(1-(4-R—C$_5$H$_9$S))] (compound IIA). First, a mixture containing compound 3A and a thiocarbonyl may be reacted at a suitable temperature for a suitable period of time, such as, for example, by heating the mixture at a temperature of about 100° C., allowing the mixture to incubate at ambient temperature (e.g., about 30° C.), etc. In this process, the thiocarbonyl compound, such as dimethylthioformamide (Me$_2$NCHS) replaces the diazonium moiety (N$_2^+$) of compound 3A to make a protected mercaptan intermediate, such as [closo-1-CB$_9$H$_8$-1-COOH-10-(1-SCHNMe$_2$)] (compound 4). Virtually any thiocarbonyl may be used in this process, although different mercaptan intermediates will be produced by the reaction of different thiocarbonyls with compound 3A. Once formed, the intermediate compound 4 may be used to synthesize Class IIA compounds. Reacting compound 4 with RCH(CH$_2$CH$_2$X)$_2$, where X is a halogen, and preferably bromine, in the presence of a base under hydrolytic conditions causes an alkylative cyclization reaction that forms Class IIA compounds. As discussed above with respect to the Class II compounds generally, R may be H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or R may be a group that, in conjunction with the compound to which it is attached (i.e., the sulfonium ring), forms an ether, a ketone, an ester, a thioester, a sulfide, or a sulfone.

Figure 5:
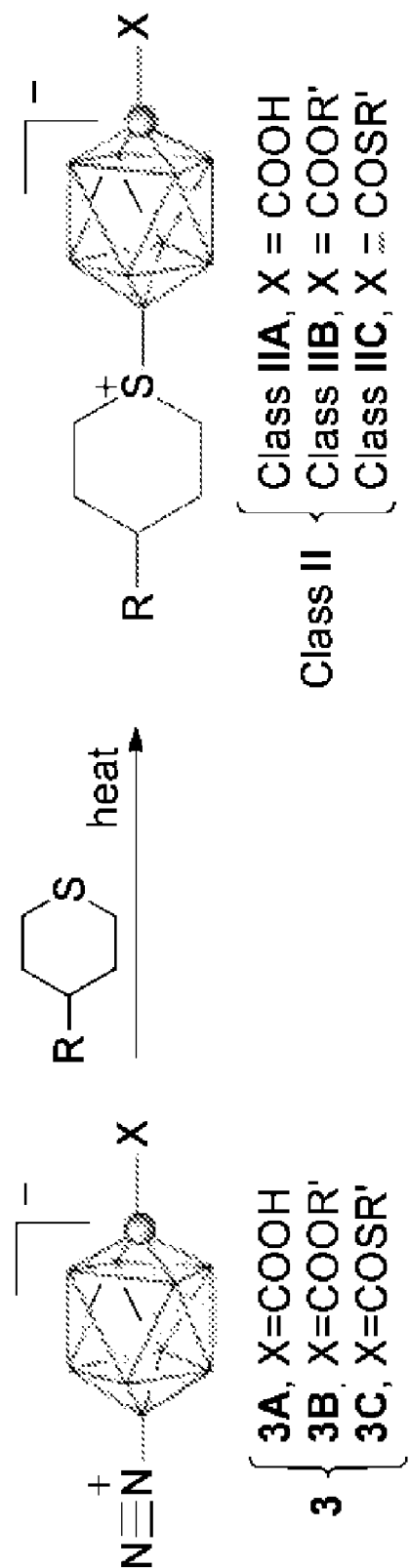
FIG. 5 is a flow chart showing the synthesis of [closo-1-CB$_9$H$_8$-1-COOH-10-(1-(4-R—C$_5$H$_9$S))], [closo-1-CB$_9$H$_8$-1-COOR'-10-(1-(4-R—C$_5$H$_9$S))] and [closo-1-CB$_9$H$_8$-1-COSR'-10-(1-(4-R—C$_5$H$_9$S))] from [closo-1-CB$_9$H$_8$-1-COOH-10-N$_2$], [closo-1-CB$_9$H$_8$-1-COOR'-10-N$_2$], and [closo-1-CB$_9$H$_8$-1-COSR'-10-N$_2$], respectively.

As shown in FIG. 5, Class II compounds also may be synthesized by heating a mixture comprising a selected compound 3 (i.e., [closo-1-CB$_9$H$_5$-1-X-10-N$_2$]) and a desired cyclic thioester derivative (e.g., 4-R—C$_5$H$_9$S) at, for example, a temperature of about 100° C., although the reaction may be heated at any suitable temperature for a suitable period of time. In this process, a sulfonium moiety replaces the diazonium moiety of compound 3 to form the Class II compound [closo-1-CB$_9$H$_5$-1-X-10-(1-(4-R—C$_5$H$_9$S))]. For example, if compound 3 is compound 3A (X=COOH), 3B (X=COOR'), or 3C (X=COSR'), then the thermolysis reaction with the cyclic thioester derivative (4-R—C$_5$H$_9$S) will form a Class IIA compound [closo-1-CB$_9$H$_5$-1-COOH-10-(1-(4-R—C$_5$H$_9$S))], a Class IIB compound [closo-1-CB$_9$H$_5$-1-COOR'-10-(1-(4-R—C$_5$H$_9$S))], or a Class IIC compound [closo-1-CB$_9$H$_5$-1-COSR'-10-(1-(4-R—C$_5$H$_9$S))], respectively. It should be appreciated that the Class IIA, IIB and IIC compounds collectively are referred to herein as [closo-1-CB$_9$H$_5$-1-X-10-(1-(4-R—C$_5$H$_9$S))], where X is COOH, COOR' or COSR', or in the alternative as "Class II compounds."

Figure 6:
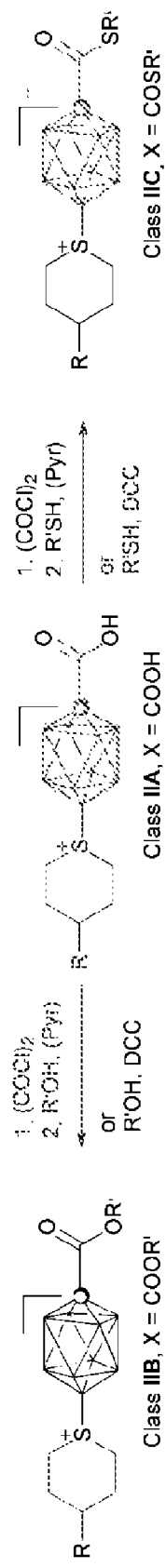
FIG. 6 is a flow chart showing the synthesis of [closo-1-CB$_9$H$_8$-1-COOR'-10-(1-(4-R—C$_5$H$_9$S))] and [closo-1-CB$_9$H$_8$-1-COSR'-10-(1-(4-R—C$_5$H$_9$S))] from [closo-1-CB$_9$H$_8$-1-COOH-10-(1-(4-R—C$_5$H$_9$S))].

As shown in FIG. 6, Class IIA compounds formed either by the cyclization reaction of FIG. 4 or the thermolysis reaction of FIG. 5 subsequently may be esterified or thioesterified with alcohol or phenol R'OH or their mercapto analogues R'SH under typical conditions to form the Class IIB and IIC compounds, respectively.

Examples of Class II compounds include, but are not limited to:

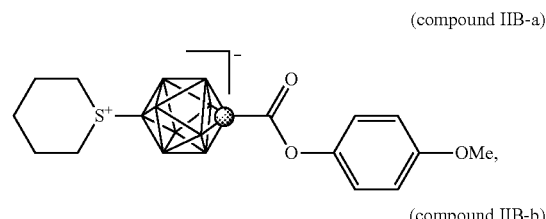
(compound IIB-a)

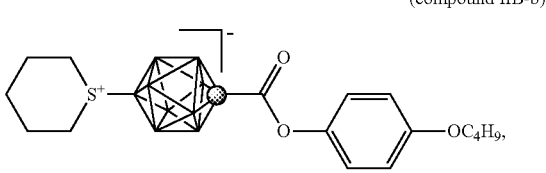
(compound IIB-b)

(compound IIB-c)

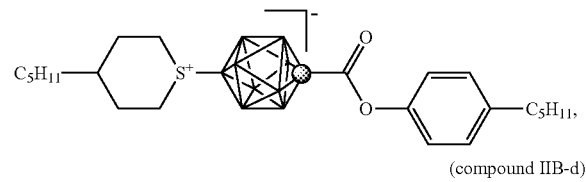
(compound IIB-d)

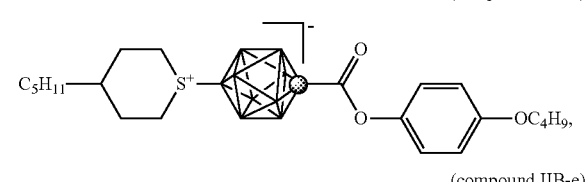
(compound IIB-e)

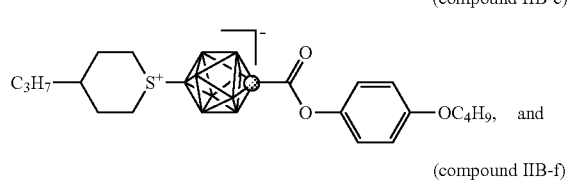
(compound IIB-f)

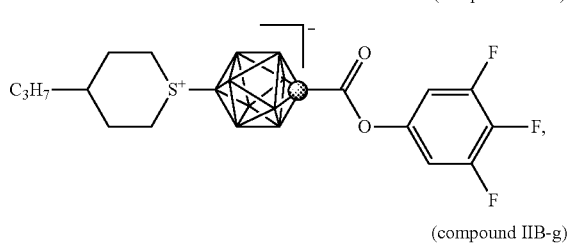
(compound IIB-g)

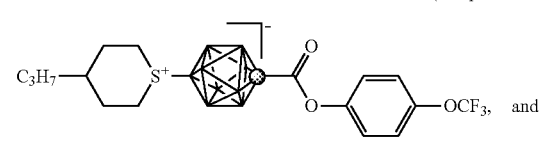

-continued (compound IIB-h)

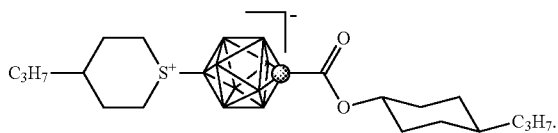

III. Class III Compounds—The Zwitterions [closo-1-CB$_9$H$_8$-1-(1-(4-R—C$_5$H$_9$S))-10-R']

The present disclosure provides, among other things, 1,10-disubstituted derivatives of the [closo-1-CB$_9$H$_{10}$]$^-$ cluster having the following structure:

Class III Compounds

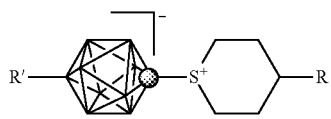

wherein R may be H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or where R may be a group that forms an ether, a ketone, an ester, a thioester, a sulfide, or a sulfone; and where R' may be H, an alkyl, a cycloalkyl, a bicycloalkyl, an alkenyl, a cycloalkenyl, a bicycloalkenyl, an alkynyl, an aryl, an alkylaryl, or a halogen. Examples of suitable R' substituents for Class III compounds include, but are not limited to, a halogen (preferably iodine or bromine), a C$_2$-C$_9$ alkyl (e.g., a propyl, a hexyl, a heptyl, an aryl substituted alkyl, a cycloalkyl substituted alkyl, etc.), and a C$_2$-C$_9$ alkenyl (e.g., butenyl, henxenyl, etc.), among others. Examples of suitable R substituents for Class III compounds include, but are not limited to a C$_2$-C$_9$ alkyl (e.g., a propyl, a pentyl, a heptyl, an aryl substituted ethyl, a cycloalkyl substituted ethyl, etc.), a C$_2$-C$_9$ alkenyl (e.g., a propenyl, a pentenyl, a heptenyl, an aryl substituted ethenyl, a cycloalkyl substituted ethenyl etc.), a C$_6$-C$_8$ cycloalkyl (e.g., a substituted or unsubstituted cyclohexyl, a substituted or unsubstituted bicyclic[2.2.2]octyl, etc.), and a substituted or unsubstituted aryl (e.g., a phenyl, an alkyl phenyl, an alkenyl phenyl, an alkoxy phenyl, a halogen substituted phenol, etc.), such as the following compounds, among others:

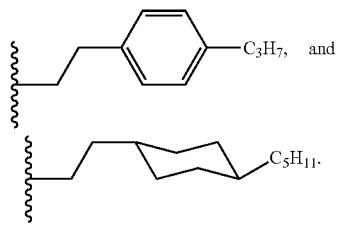

Class III compounds may have a longitudinal component of the molecular dipole moment exceeding about 14 Debye. Like the Class I and II compounds discussed above, the large longitudinal component of the molecular dipole moment for the Class III compounds originates from the zwitterionic structure. Also like the Class I and II compounds, the Class III compounds generally may have a melting point that is above ambient temperatures. Specific properties of the Class III compounds, such as melting temperatures, formation of liquid crystalline phases, phase range, and also miscibility with other liquid crystals or nematic hosts, depend on the specific identity of the substituents R and R', as discussed in the Examples.

Figure 7:
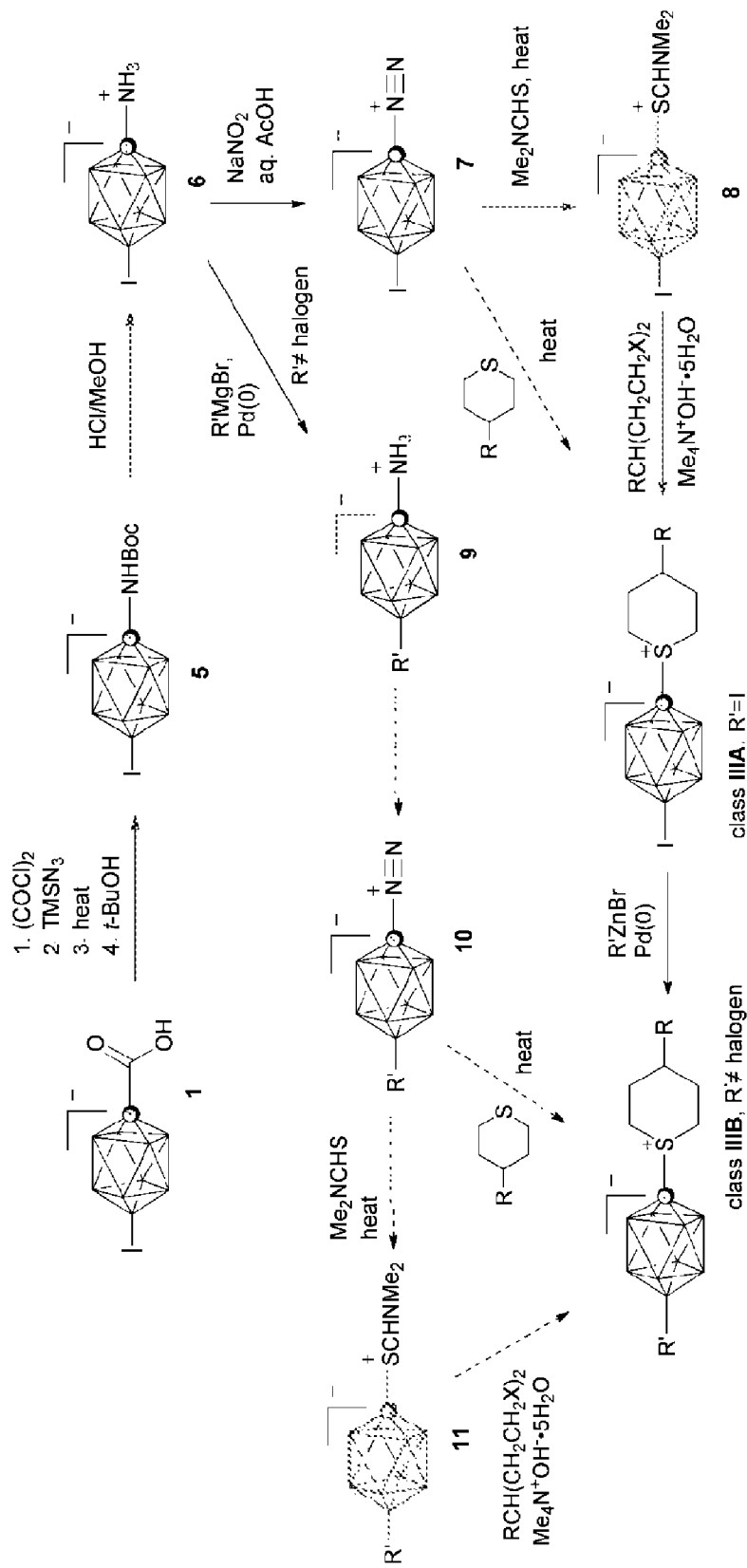
FIG. 7 is a flow chart showing the synthesis of [closo-1-CB$_9$H$_8$-1-(1-(4-R—C$_5$H$_9$S))-10-I] and [closo-1-CB$_9$H$_8$-1-(1-(4-R—C$_5$H$_9$S))-10-R'] from [closo-1-CB$_9$H$_8$-1-COOH-10-I]$^-$.

FIG. 7 is a flow chart showing the general synthesis of Class III compounds. Specifically, it shows the various methods of making Class III compounds from [closo-1-CB$_9$H$_8$-1-COOH-10-I]$^-$ (compound 1). First, a modified Curtius reaction may be used to prepare the Boc protected amine [closo-1-CB$_9$H$_8$-1-NHBoc-10-I]$^-$ (compound 5). Compound 5 functions as a convenient and generally stable means for storing the amine [closo-1-CB$_9$H$_8$-1-NH$_3$-10-I]$^-$ (compound 6), which is formed by deprotecting compound 5 with acid, such as HCl. Multiple processes can be used to synthesize Class III compounds from compound 6. Some of these processes involve the synthesis of a diazonium derivative of the [closo-1-CB$_9$H$_{10}$]$^-$ cluster [closo-1-CB$_9$H$_8$-1-N$_2$-10-I]$^-$ (compound 7), which is synthesized by diazotization of compound 6 with NaNO$_2$. Multiple processes also can be used to synthesize Class III compounds from compound 7.

In some processes, a mixture containing compound 7 and a thiocarbonyl may be reacted at a suitable temperature for a suitable period of time, such as, for example, by heating the mixture at a temperature of about 100° C., allowing the mixture to incubate at ambient temperature (e.g., about 30° C.), etc. In this process, the thiocarbonyl compound, such as dimethylthioformamide (Me$_2$NCHS) replaces the diazonium moiety (N$_2^+$) of compound 7 to make a mercaptan protected intermediate, such as [closo-1-CB$_9$H$_8$-1-(1-SCHNMe$_2$)-10-I] (compound 8). Virtually any thiocarbonyl may be used in this process, although different mercaptan intermediates will be produced by the reaction of different thiocarbonyls with compound 7. Once formed, the intermediate compound 8 may be used to synthesize [closo-1-CB$_9$H$_8$-1-(1-(4-R—C$_5$H$_9$S))-10-I], which hereinafter is referred to as a Class IIIA compound, although it should be appreciated that Class IIIA compounds may have any halogen in place of iodine, namely, by using [closo-1-CB$_9$H$_8$-1-COOH-10-halogen]$^-$, in place of compound 1 in the early stages of the synthesis. Compound 8 may be reacted with RCH(CH$_2$CH$_2$X)$_2$, where X is a halogen, and preferably bromine, in the presence of a base under hydrolytic conditions, which causes an alkylative cyclization reaction that forms a Class IIIA compound. As discussed above with respect to the Class III compounds generally, R may be H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or R may be a group that, in conjunction with the compound to which it is attached (i.e., the sulfonium ring), forms an ether, a ketone, an ester, a thioester, a sulfide, or a sulfone. The Class IIIA compound may then subsequently be used to form a Class IIIB compound [closo-1-CB$_9$H$_8$-1-(1-(4-R—C$_5$H$_9$S))-10-R'], where R'≠halogen, by reacting the Class IIIA compound with an organometallic reagent, such as R'ZnBr in the presence of a catalyst, such as palladium. In this process for synthesizing the Class IIIB compounds, R' may be an alkyl, a cycloalkyl, a bicycloalkyl, an alkenyl, a cycloalkenyl, a bicycloalkenyl, an alkynyl, an aryl, an alkylaryl.

In some processes, Class III compounds may be synthesized by reacting a mixture comprising compound 7 (i.e., [closo-1-CB$_9$H$_8$-1-N$_2$-10-I]) and a desired cyclic thioester derivative (e.g., 4-R—C$_5$H$_9$S) at a suitable temperature for a suitable period of time such as, for example, by heating the mixture at a temperature of about 100° C., or allowing the mixture to incubate at ambient temperature (e.g. about 30° C.), etc. In this process, a sulfonium moiety replaces the diazonium moiety of compound 7 to form the Class IIIA compound [closo-1-CB$_9$H$_8$-1-(1-(4-R—C$_5$H$_9$S))-10-I]. Once again, R may be H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or R may be a group that, in conjunction with the compound to which it is attached (i.e., the sulfonium ring), forms an ether, a ketone, an ester, a thioester, a sulfide, or a sulfone. As with other processes described above, the Class IIIA compound can be used to make a Class IIIB compound in the manner described above.

In yet other processes, compound 6 (i.e., [closo-1-CB$_9$H$_8$-1-NH$_3$-10-I]) may be used to form [closo-1-CB$_9$H$_8$-1-NH$_3$-10-R'] (compound 9), where R' may be an alkyl, a cycloalkyl, a bicycloalkyl, an alkenyl, a cycloalkenyl, a bicycloalkenyl, an alkynyl, an aryl, an alkylaryl. Specifically, compound 6 may be reacted with an organometallic reagent, such as R'MgBr or R'ZnBr in the presence of a catalyst, such as palladium, to form compound 9. Compound 9 then may be reacted with NaNO$_2$ or Na$^+$BF$_4$— to form [closo-1-CB$_9$H$_8$-1-N$_2$-10-R'] (compound 10) via a diazotization reaction. A mixture containing compound 10 and a thiocarbonyl then may be reacted at a suitable temperature for a suitable period of time such as, for example, by heating the mixture at a temperature of about 100° C., or allowing the mixture to incubate at ambient temperature (e.g., about 30° C.), etc. In this process, the thiocarbonyl compound, such as dimethylthioformamide (Me$_2$NCHS) replaces the diazonium moiety (N$_2^+$) of compound 10 to form a mercaptan protected intermediate, such as [closo-1-CB$_9$H$_8$-1-(1-SCHNMe$_2$)-10-R'] (compound 11). As with similar processes discussed above, virtually any thiocarbonyl may be used in this process, although different mercaptan intermediates will be produced by the reaction of different thiocarbonyls with compound 10. Once formed, the intermediate compound 11 may be used to synthesize Class IIIB compounds via the cyclization reaction with RCH(CH$_2$CH$_2$X)$_2$, where X is a halogen, and preferably bromine, in the presence of a base under hydrolytic conditions. In these processes, R may be H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or where R may be a group that forms an ether, a ketone, an ester, a thioester, a sulfide, or a sulfone.

In yet other processes, Class IIIB compounds may be synthesized directly from compound 10 by reacting a mixture comprising compound 10 and a desired cyclic thioester derivative (e.g., 4-R—C$_5$H$_9$S) at a suitable temperature for a suitable period of time, such as, for example, by heating the mixture at a temperature of about 100° C., or allowing the mixture to incubate at ambient temperature (e.g., at about 30° C.), etc. In this process, a sulfonium moiety replaces the diazonium moiety of compound 10 to form the Class IIIB compound. Once again, R may be H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or R may be a group that, in conjunction with the compound to which it is attached (i.e., the sulfonium ring), forms an ether, a ketone, an ester, a thioester, a sulfide, or a sulfone.

It should be appreciated that the Class IIIA and IIIB compounds collectively may be referred to herein as [closo-1-CB$_9$H$_8$-1-(1-(4-R—C$_5$H$_9$S))-10-R'], as is generally defined above, or in the alternative as "Class III compounds."

Examples of Class III compounds include, but are not limited to:

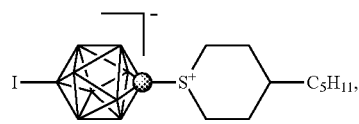
(compound IIIA-a)

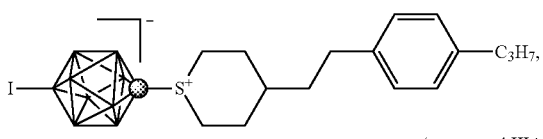
(compound IIIA-b)

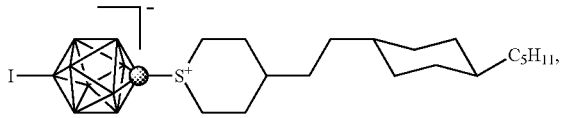
(compound IIIA-c)

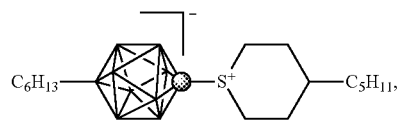
(compound IIIB-a)

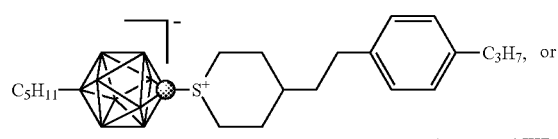
(compound IIIB-b)

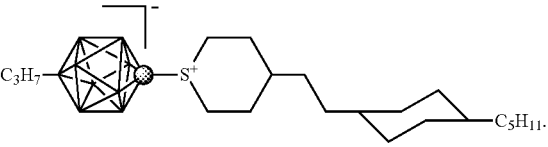
(compound IIIB-c)

IV. Articles of Manufacture Comprising the Class I-III Compounds

The Class I-III compounds disclosed herein may be used as components of various articles of manufacture, including mixtures of liquid crystals, and devices having liquid crystal displays that utilize such mixtures.

The Class I-III compounds specifically may be used as additives of liquid crystalline materials that change the properties of the materials, such as the dielectric permittivity, phase transition temperatures, and the like. For example, one or more Class I-III compounds may be used as components of binary or multi-component mixtures containing one or more nematic hosts, one or more other polar compounds, one or more other additives, and the like.

A nematic host or host mixture may be selected based on the intended use of the mixture. Numerous nematic hosts exists, and any such nematic host may be used to form a mixture comprising a Class I-III compound. Suitable nematic hosts or host mixtures include, but are not limited to, one or more azoxybenzenes, benzylideneanilines, biphenyls, terphenyls, phenyl or cyclohexyl benzoates, phenyl or cyclohexyl esters of cyclohexanecarboxylic acid; phenyl or cyclohexyl esters of cyclohexylbenzoic acid; phenyl or cyclohexyl esters of cyclohexylcyclohexanecarboxylic acid; cyclohexylphenyl esters of benzoic acid, of cyclohexanecarboxylic acid and of cyclohexylcyclohexanecarboxylic acid; phenyl cyclohexanes; cyclohexylbiphenyls; phenyl cyclohexylcyclohexanes; cyclohexylcyclohexanes; cyclohexylcyclohexenes;

cyclohexylcyclohexylcyclohexenes; 1,4-bis-cyclohexylbenzenes; 4,4-bis-cyclohexylbiphenyls; phenyl- or cyclohexylpyrimidines; phenyl- or cyclohexylpyridines; phenyl- or cyclohexylpyridazines; phenyl- or cyclohexyldioxanes; phenyl- or cyclohexyl-1,3-dithianes; 1,2-diphenylethanes; 1,2-dicyclohexylethanes; 1-phenyl-2-cyclohexylethanes; 1-cyclohexyl-2-(4-phenylcyclohexyl)ethanes; 1-cyclohexyl-2',2-biphenylethanes; 1-phenyl-2-cyclohexylphenylethanes; optionally halogenated stilbenes; benzyl phenyl ethers; tolanes; substituted cinnamic acids and esters; and further classes of nematic or nematogenic substances. For example, suitable nematic hosts may include, but are not limited to, ClEster, 6-CHBT and ZLI-1132 (a tradename of a proprietary compound made by MERCK® of Darmstadt, Germany):

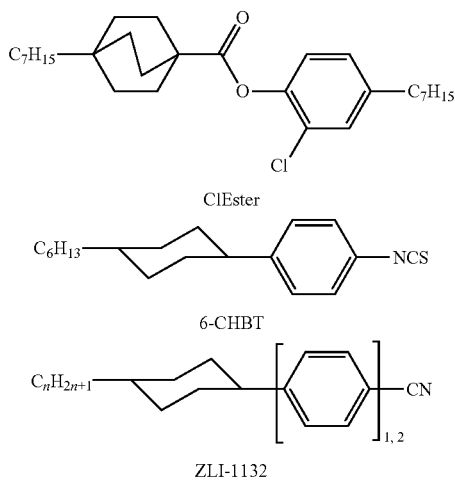

Other suitable commercial nematic liquid crystals include, but are not limited to, E7, E44, E48, E31, E80, BL087, BL101, ZLI-3308, ZLI-3273, ZLI-5048-000, ZLI-5049-100, ZLI-5100-100, ZLI-5800-000, MLC-6041-100, TL202, TL203, TL204 and TL205 (all tradename of proprietary compounds made by MERCK® of Darmstadt, Germany). Although nematic liquid crystals having positive dielectric anisotropy are preferred, virtually any nematic liquid crystal known in the art, including those having negative dielectric anisotropy should be suitable for use with Class I-III compounds. Other nematic materials also may be suitable for use in the present invention as would be appreciated by those skilled in the art.

Factors that may affect whether a particular Class I-III compound may be a useful additive for a particular host (or host mixture) include the solubility of the Class I-III compound in the particular host or host mixture, and the affects of the Class I-III compound on the physical properties of the particular host or host mixture. For example, a selected Class I-III compound preferably is soluble in the host or host mixture up to a concentration of at least about 5%, and more preferably up to concentrations of at least about 10%, at least about 30%, at least about 40%, or at least about 50%. Preferred Class I-III compounds for a particular host or host mixture will appreciably deleteriously increase the viscosity of the host, or substantially decrease the nematic-isotropic transition temperature of the host.

The Class I-III zwitterions described herein are especially useful as additives for formulation of nematic liquid crystal materials with positive dielectric anisotropy, $\Delta\epsilon > 0$. The role of the zwitterion additive may be to increase dielectric anisotropy $\Delta\epsilon$ of the material, and by doing so, decrease the threshold voltage $V_{TH}$ (i.e., the minimum voltage necessary to cause realignment of molecules in the LC materials, thereby causing an optical effect), or increase the speed of the realignment at the given voltage above $V_{TH}$. As such, specific nematic mixtures may be formulated with specific Class I-III compounds for a specific type of LCD. Class I-III compounds selected for use with a particular host preferably increase the anisotropy of dielectric permittivity of a nematic host at least about 0.5, such as at least about 1, at least about 2, or at least about 4.

An optimal Class I-III compound for a particular host or host mixture will increase the anisotropy of dielectric permittivity a desired amount with the least amount of compound added, such as at optimal concentrations of less than about 20%, less than about 10%, less than about 5%, or between about 3% and about 10%. The optimal concentration will depend on the initial $\Delta\epsilon$ of the nematic host and the target $\Delta\epsilon$ of the final mixture. The optimal concentration also may depend on specific host-additive interactions that may cause the final mixture to have different viscosity or elastic constants than the nematic host alone. Some increase of viscosity is tolerable but high viscosity is detrimental for most (but not all) applications. Finally, the optimal concentration will depend on the solubility of the additive in the nematic host and the impact the additive has on phase transition temperatures.

As discussed above, mixtures comprising one or more Class I-III compounds and one or more nematic hosts may also include one or more other polar compounds and/or one or more other additives. These other polar compounds and/or additives may be selected to modify the mixture's properties, such as birefringence (i.e. optical anisotropy), dielectric anisotropy, viscosity, elastic constants, transition temperatures, etc.

The Class I-III compounds disclosed herein also may be used as components of devices having liquid crystal displays (LCDs). As used herein, a "liquid crystal display" (LCD) is a type of flat panel display used in various electronic devices including, but not limited to, television sets, laptop computers, computer monitors, hand-held communication devices, gaming devices, watches, cash registers, clocks, and/or calculators. At a minimum, an LCD comprises a substrate, at least one conductive layer and a liquid crystal layer. The liquid crystal (LC) is used as an optical switch. The substrates are usually manufactured with transparent, conductive electrodes, in which electrical "driving" signals are coupled. The driving signals induce an electric field which can cause a phase change or state change in the liquid crystal material, the liquid crystal exhibiting different light reflecting characteristics according to its phase and/or state. Liquid crystals comprising Class I-III compounds may be used with virtually any type of LCD.

Examples of nematic hosts, additives, mixtures prepared with nematic hosts and additives, and LCDs comprising nematic compounds and nematic mixtures, are disclosed in U.S. Pat. Nos. 7,258,902; 7,294,369; 7,318,950; 7,333,166; 7,372,530; 7,382,424; 7,387,856; 7,387,858; 7,394,506; 7,410,825; 7,414,313; 7,416,684; 7,425,356; 7,427,441; 7,438,832; 7,440,160; 7,442,475; 7,445,819; 7,452,482; 7,452,575; 7,465,479; 7,470,376; 7,473,448; 7,482,044; 7,507,449; 7,531,106; 7,532,290; 7,553,522; 7,557,875; 7,563,389; 7,563,491; 7,564,528; 7,579,053; 7,583,834; 7,630,029; 7,638,780; 7,642,035; 7,645,497; 7,675,594; 7,682,671; 7,691,455; 7,704,568; 7,710,522; 7,740,918; 7,754,295;

7,771,800; 7,771,801; 7,781,047; 7,794,621; 7,812,919, the complete disclosures of which are herein incorporated by reference for all purposes.

EXAMPLES

Example 1

Synthesis of [closo-1-CB$_9$H$_8$-1-COO-10-NH$_3$]$^-$ NMe$_4^+$ (Compound 2•[NMe$_4$])

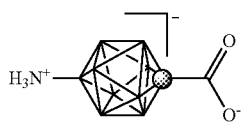

A solution was prepared by adding [closo-1-CB$_9$H$_8$-1-COOH-10-I]$^-$NMe$_4^+$ (compound 1•[NMe$_4$]) (1.00 g, 2.75 mmol) to a solution of lithium hexamethyldisilazane (LiHMDS, 41.2 mL, 41.3 mmol, 1.0 M in THF) at room temperature under Ar, which formed a light orange suspension. The suspension was stirred vigorously for 15 min., or until the suspension became more fine and disperse. Pd$_2$dba$_3$ (0.050 g, 0.055 mmol) and 2-(dicyclohexylphosphino)biphenyl (0.077 g, 0.22 mmol) were added, and the reaction was stirred at reflux for 20 hr. After several minutes at reflux, the reaction mixture turned dark brown. The reaction was cooled to 0° C., and 10% HCl (100 mL) was added slowly. The THF was removed in vacuo giving a dark orange solution. The orange solution was extracted with Et$_2$O (3×30 mL), the Et$_2$O layers were combined, dried (Na$_2$SO$_4$), and evaporated at slightly elevated temperature (~40° C.) to ensure complete removal of trimethylsilanol. $^{11}$B NMR of the crude brown/orange material revealed a 70:30 ratio of amino acid compound 2 to compound 1•[NMe$_4$].

The crude brown/orange material was re-dissolved in Et$_2$O, and then H$_2$O (10 mL) was added. The Et$_2$O was removed in vacuo or until bubbling became less vigorous. The aqueous layer was filtered, and the process was repeated two more times. The aqueous layers were combined, and NEt$_4^+$Br$^-$ ((0.578 g, 2.75 mmol) was added resulting in precipitation of a white solid. CH$_2$Cl$_2$ (20 mL) was added, and the biphasic system was stirred vigorously until the H$_2$O layer became clear (~30 mins). The CH$_2$Cl$_2$ was separated, and the process was repeated once more. The H$_2$O layer was filtered, re-acidified with concentrated HCl (5 mL), and extracted with Et$_2$O (3×10 mL). The Et$_2$O layers were combined, washed with H$_2$O, dried (Na$_2$SO$_4$), and evaporated giving 0.260 g of compound 2 with a purity >90% by $^{11}$B NMR.

A solution was prepared by dissolving 0.194 g (1.08 mmol) of crude compound 2 in CH$_3$OH (5 mL). 0.180 g and NMe$_4^+$OH$^-$.5H$_2$O (0.993 mmol) was added. The mixture was stirred for 1 hr, CH$_3$OH was removed in vacuo, and the residue was washed with Et$_2$O and then with boiling MeCN (2×) to give 0.221 g (88% recovery, 44% overall yield) of pure compound 2•[NMe$_4$] as a fluffy off-white solid having a melting point >260° C.

Example 2

Synthesis of [closo-1-CB$_9$H$_8$-1-COOH-10-NH$_3$] (Compound 2)

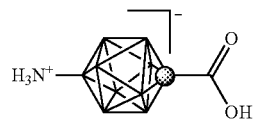

A solution was prepared by dissolving 0.055 g (0.22 mmol) of compound 2•[NMe$_4$] in 10% HCl (2 mL), and the solution was extracted with ether (3×2 mL). The organic layers were combined, washed with H$_2$O (2 mL), and dried (Na$_2$SO$_4$), and the solvent was evaporated, forming a white solid residue. The residue was dried in vacuum to give 0.039 g (~100% yield) of pure compound 2 as a white solid having a melting point of >260° C.

Example 3

Synthesis of [closo-1-CB$_9$H$_8$-1-COOH-10-N$_2$] (Compound 3A)

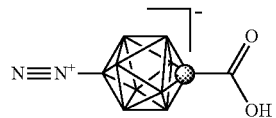

A suspension was prepared by adding 0.105 g (0.59 mmol) of Compound 2 to anhydrous CH$_3$CN (2 mL) under Ar. Anhydrous pyridine (0.240 mL, 2.93 mmol) was added, and the mixture was sonicated for 5 min. The reaction mixture was cooled to −15° C., and nitrosonium hexafluorophosphate (NO$^+$PF$_6^-$, 0.310 g, 1.77 mmol) was added in five portions at 5 minute intervals. Addition of NO$^+$PF$_6^-$ resulted in a green/blue homogeneous solution that slowly faded to colorless. The solution then became more yellow as more NO$^+$PF$_6^-$ was introduced. Once all the NO$^+$PF$_6^-$ was added, the reaction mixture was stirred for 1.5 hr at −15° C.

The reaction mixture was evaporated to dryness while the flask was kept in a cold water bath. 10% HCl (10 mL) was then added, and the mixture was stirred vigorously until all solids had dissolved (~20 min). The aqueous solution was extracted with Et$_2$O (3×5 mL), and the Et$_2$O layers were combined, washed with H$_2$O, dried (Na$_2$SO$_4$), and evaporated to dryness, giving 0.107 g of crude compound 3A. The crude product was passed through a short silica gel plug (CH$_3$OH/CH$_2$Cl$_2$, 1:19, R$_f$=0.2) giving 0.087 g (78% yield) of compound 3A as a white solid, which was recrystallized from aqueous MeOH containing a few drops of acetone. Compound 3A had a melting point of 174-177° C.

Example 4

Synthesis of [closo-1-CB$_9$H$_8$-1-COOH-10-(1-NC$_5$H$_5$)] (Compound IA-a)

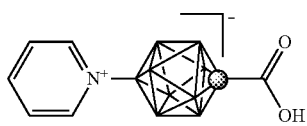

A slight yellow solution of Compound 3A (0.048 g, 0.25 mmol) and anhydrous pyridine (3.0 mL, 37.1 mmol) was stirred at 100° C. for 1 hr. As the reaction progressed, bubbling of N$_2$ became evident. Excess pyridine was removed in vacuo, 10% HCl (10 mL) was added to the residue, and the solution was extracted with Et$_2$O (3×5 mL). The Et$_2$O layers were combined, washed with H$_2$O, dried (Na$_2$SO$_4$), and evaporated giving 0.060 g of crude compound IA-a as a slight yellow solid. The crude compound IA-a was passed through a short silica gel plug (CH$_3$OH/CH$_2$Cl$_2$, 1:19, R$_f$=0.4) giving 0.054 g (90% yield) of compound IA-a as an off-white solid, which was further purified by recrystallization from EtOH/H$_2$O (3×). Compound IA-a had a melting point of 258-260° C.

Example 5

Synthesis of [closo-1-CB$_9$H$_8$-1-COOH-10-(1-(4-C$_7$H$_{15}$O)—C$_5$H$_4$N)] (Compound IA-b)

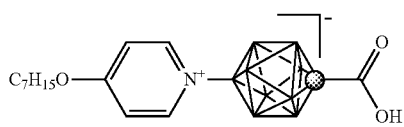

Compound IA-b was prepared to an 88% yield using the same process described for compound IA-a above, except starting from a solution of compound 3A (0.095 g, 0.50 mmol) and 4-heptyloxypyridine (3.0 mL). A small portion of the product was passed through a cotton plug and recrystallized from aq. EtOH (4×) giving an analytical sample having a melting point of 208-210° C.

Example 6

General Procedures for the Synthesis of Class IB and IC Compounds

Method A. Red/orange solutions containing 0.25 mmol of a Class IA compound [closo-1-CB$_9$H$_8$-1-COOH-10-(1-(4-R—C$_5$H$_4$N))], 0.28 mmol of an alcohol or phenol (R'OH) or a mercaptan (R'SH), 0.25 mmol DMAP, and 0.25 mmol 2-chloro-3,5-dinitropyridine in 1 mL anhydrous pyridine may be stirred at reflux under Ar. Reaction progress may be monitored by $^1$H NMR of a small aliquot in CD$_3$CN. If the reaction is incomplete, additional equivalents of CDNP may be added and heating continued (6-48 hrs). Excess pyridine may be removed to dryness giving a red/orange crystalline film. The film may be treated with 10% HCl and extracted into Et$_2$O (3×). The Et$_2$O layers may be combined, washed with a saturated solution of NaHCO$_3$, dried (Na$_2$SO$_4$), and evaporated. The crude product may be further purified by passage through a short silica gel plug (CH$_2$Cl$_2$/hexane mixture), filtered through a cotton plug, and recrystallized.

Method B. A suspension of a Class IA compound (0.25 mmol) and anhydrous CH$_2$Cl$_2$ (1 mL) may be treated with a 0.5 M solution of (COCl)$_2$ in CH$_2$Cl$_2$ (0.75 mL, 0.375 mmol) and 0.1 M solution of anhydrous DMF in CH$_2$Cl$_2$ (0.25 mL, 0.025 mmol) at room temperature. The mixture will began to bubble, and the reaction will became homogeneous. After 30 mins, the light yellow solution of the resulting acid chloride derived from the Class IA compound may be evaporated to dryness, and redissolved in anhydrous CH$_2$Cl$_2$ (1 mL), and alcohol, phenol, or mercaptan (1.5 equivalents) and a 0.5 M solution of freshly distilled NEt$_3$ in CH$_2$Cl$_2$ (0.25 mL, 0.75 mmol) may be added. The reaction may be stirred overnight at room temperature, evaporated to dryness, passed through a short silica gel plug (CH$_2$Cl$_2$/hexane mixture), filtered through a cotton plug, and recrystallized.

Method C. An acid chloride derived from a Class IA compound (0.25 mmol) may be generated as in Method B. Without purification, the chloride, excess alcohol (~1 mmol), and freshly distilled pyridine (0.1 mL) may be added. The mixture may be heated for 3 days at 90° C. protected from moisture. At times, the reaction may be cooled to room temperature, and minimal anhydrous CH$_2$Cl$_2$ may be added to wash the sides of the flask. The product may be purified as in Method B.

NMR spectra, $^1$H NMR (400 MHz, CDCl$_3$, 25° C., CHCl$_3$) and $^{11}$B NMR (128.4 MHz, CDCl$_3$, 25° C., B(OH)$_3$/MeOH), recorded for all compounds are consistent with their chemical structures. Combustion and thermal analyses demonstrated high purity of the compounds.

Example 7

Synthesis of Ester Formed from [closo-1-CB H-1-COOH-10-(1-NC$_5$H$_5$)] and Cyclohexanol (Compound IB-a)

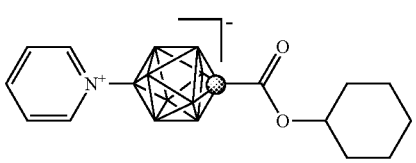

Compound IB-a was synthesized using Method A of Example 5. The crude product was further purified by passing through a short silica gel plug (hexane/CH$_2$Cl$_2$; 3:7). The eluent was filtered through a cotton plug, and the product was recrystallized (5×) from iso-octane/toluene mixtures in the freezer. Ester IB-a was obtained in 75% yield as colorless blades (R$_f$=0.5 in CH$_2$Cl$_2$).

Example 8

Synthesis of Ester Formed from [closo-1-CB$_9$H$_8$-1-COOH-10-(1-(4-C$_7$H$_{15}$O)—C$_5$H$_4$N)] and 4-pentyl-bicyclo[2.2.2]octan-1-ol (Compound IB-b)

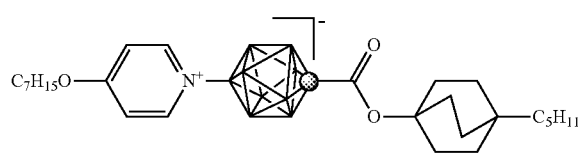

Compound IB-b was synthesized using Method C of Example 5. Compound IB-b was isolated in 9% yield after chromatography (CH$_2$Cl$_2$/hexane, 3:7) and was recrystallized from iso-octane/toluene (4×) giving colorless leaflets having a melting point of 161° C. (DSC).

Example 9

Synthesis of Ester Formed from [closo-1-CB$_9$H$_8$-1-COOH-10-(1-(4-C$_7$H$_{15}$O—C$_5$H$_4$N))] and 4-trans-pentylcyclohexanol (Compound IB-c)

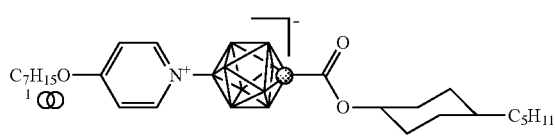

Compound IB-c was synthesized using Method C of Example 5. Compound IB-c was isolated in 40% yield after chromatography (CH$_2$Cl$_2$/hexane, 3:7) and was recrystallized from iso-octane/toluene (5×) at −20° C. giving colorless leaflets.

Example 10

Synthesis of Ester Formed from [closo-1-CB$_9$H$_8$-1-COOH-10-(4-C$_7$H$_{15}$O—C$_5$H$_4$N)] and p-pentylphenol (Compound IB-d)

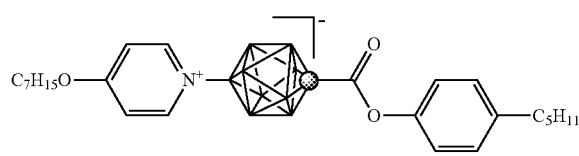

Compound IB-d was synthesized using Method A of Example 5. Peaks at 2.66 ppm and 4.34 ppm in $^1$H NMR (CD$_3$CN) were monitored until the desired 1:1 ratio was achieved. Compound IB-d was isolated in 64% yield after chromatography (CH$_2$Cl$_2$/hexane, 3:7) and purified by recrystallization from iso-octane/toluene (5×) at −20° C. giving colorless leaflets.

Example 11

Synthesis of Ester Formed from [closo-1-CB$_9$H$_8$-1-COOH-10-(1-(4-C$_7$H$_{15}$O—C$_5$H$_4$N))] and 4-butoxyphenol (Compound IB-e)

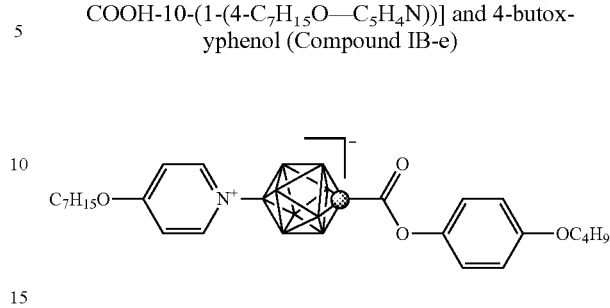

Compound IB-e was synthesized using Method B of Example 5. The yield after chromatography (CH$_2$Cl$_2$/hexane, 3:7) was 79%. Compound IB-e was purified by recrystallization from aqueous EtOH (3×) at room temperature giving colorless leaflets.

Example 12

Synthesis of Ester Formed from [closo-1-CB$_9$H$_8$-1-COOH-10-(1-(4-C$_7$H$_{15}$O—C$_5$H$_4$N))] and 4-cyanophenol (Compound IB-f)

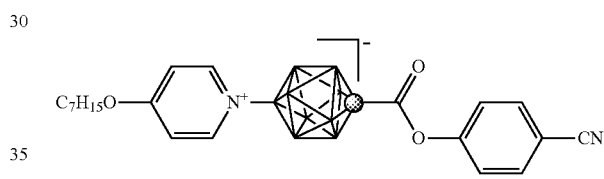

Compound IB-f It was synthesized using Method B of Example 5. The yield after chromatography (CH$_2$Cl$_2$/hexane, 1:1) was 91%. Compound IB-f was purified by washing with boiling pentane (2×) and recrystallization from aq. EtOH (1×) at −20° C., CH$_3$OH (1×) at −20° C., and CH$_3$OH (1×) at −40° C. giving colorless blades.

Example 13

Synthesis of [closo-1-CB$_9$H$_8$-1-COOH-10-SCHN(CH$_2$)$_3$] (Compound 4)

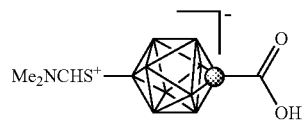

A solution of 0.061 g (0.32 mmol) Compound 3A and freshly distilled Me$_2$NCHS (3.0 mL, 35.2 mmol) was stirred at 100° C. for 1 hr. As the reaction progressed, bubbling of N$_2$ became evident. Excess Me$_2$NCHS was removed by vacuum distillation (95° C., 1.5 mm Hg) leaving an off-white crystalline crude product. The crude product was washed with toluene giving 0.076 g (95% yield) of crude protected mercaptan Compound 4 containing ~5% of Me$_2$NCHS by $^1$H NMR. The melting point of Compound 4 was 250-253° C. dec.

Example 14

General Procedure for the Synthesis of Class IIA Compounds

An about 0.26 mmol solution of Compound 4 in anhydrous $CH_3CN$ (4 mL) may be treated with a solution of $NMe_4^+OH^-$ .$5H_2O$ (about 1.3 mmol) in anhydrous $CH_3CN$ (6 mL), which results in the formation of a white precipitate. An appropriate 3-substituted 1,5-dibromopentane $RCH(CH_2CH_2Br)_2$ (about 0.26 mmol) may be added and the reaction mixture may be stirred for 24 hrs at room temperature. The reaction mixture may be evaporated to dryness and stirred in a methanol solution (4 mL) of NaOH (0.01 g, 0.250 mmol) at 50° C. for 4 hrs, to hydrolyze small amounts of ester. Solvent may be removed to dryness and 10% HCl (10 mL) may be added. The suspension may be stirred vigorously with $Et_2O$ (5 mL) until the aqueous layer became homogeneous. The $Et_2O$ layer may be separated, and the aqueous layer further may be extracted with $Et_2O$ (2×5 mL). The $Et_2O$ layers may be combined, washed with $H_2O$, dried ($Na_2SO_4$), and evaporated leaving a crude Class IIA compound as an orange-yellow crystalline film. The crude Class IIA compound may be passed through a short silica gel plug ($CH_3OH/CH_2Cl_2$) and washed with hot hexane giving compound IIA as an off-white solid. The product may be recrystallized from aqueous EtOH and then from toluene to give pure product.

Example 15

Synthesis of [closo-1-$CB_9H_5$-1-COOH-10-(1-$SC_5H_{10}$)] (Compound IIA-a)

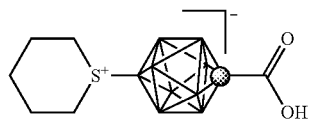

Crude compound IIA-a was synthesized using the method of Example 13 using 1,5-dibromopentane. The crude compound IIA-a was passed through a short silica gel plug ($CH_3OH/CH_2Cl_2$, 1:19, $R_f$=0.4), and washed with hot hexane giving 54% yield of IIA-a as an off-white solid. Recrystallization from aqueous EtOH and then from toluene, and subsequent drying at 100° C. in vacuum for 2 hr gave compound IIA-a as colorless blades with a melting point of 232-233° C.

Example 16

Synthesis of [closo-1-$CB_9H_5$-1-COOH-10-(1-(4-$C_5H_{11}$)—$C_5H_9S$)] (Compound IIA-b)

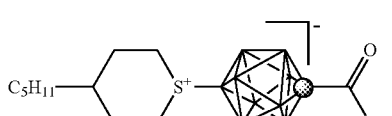

Crude compound IIA-b was synthesized using the method of Example 13 using 1,5-dibromo-3-pentyl-pentane. The crude compound IIA-b was passed through a short silica gel column ($CH_3OH/CH_2Cl_2$, 1:19, $R_f$=0.4), washed with hot hexane giving 44% yield of compound IIA-b as an off-white solid which was recrystallized twice from cold $CH_3CN$ (−20° C.), once from cold iso-octane/toluene (−20° C.), and dried in vacuo at 110° C. for 2 hr. The final product had a melting point of 215-216° C.

Example 17

Synthesis of [closo-1-$CB_9H_5$-1-COOH-10-(1-(4-$C_3H_9S$)] (Compound IIA-c)

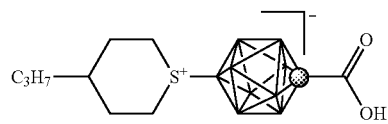

Crude compound IIA-c was synthesized using the method of Example 13 using 1,5-dibromo-3-propyl-pentane. The crude compound IIA-c was passed through a short silica gel column ($CH_3OH/CH_2Cl_2$, 1:19) and washed with hot hexane giving 43% yield of compound IIA-c. The solid was recrystallized from aqueous EtOH and then iso-octane/toluene, and dried in vacuo at 110° C. for 2 hr. The final product had a melting point of 232-233° C.

Example 18

General Procedure for Preparation of Class IIB and IIC Compounds

Class IIB and IIC compounds may be prepared according to the same general Method A and Method B described in Example 5.

Example 19

Synthesis of [closo-1-$CB_9H_8$-1-($COOC_6H_4OMe$)-10-(1-$SC_5H_{10}$)] (Compound IIB-a)

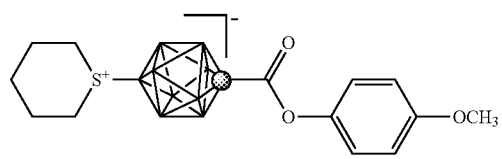

Compound IIB-a was synthesized from Compound IIA-a and p-methoxyphenol using Method A of Example 17. The ratio of peaks at 3.82 ppm and 7.01 ppm in $^1$H NMR ($CD_3CN$) was monitored until the desired 3:2 ratio was achieved. Compound IIA-a was isolated in 54% yield as colorless needles ($R_f$=0.6 in $CH_2Cl_2$).

Example 20

Synthesis of the Ester Formed from [closo-1-CB$_9$H$_8$-1-COOH-10-C$_5$H$_{10}$S] and 4-butoxyphenol (Compound IIB-b)

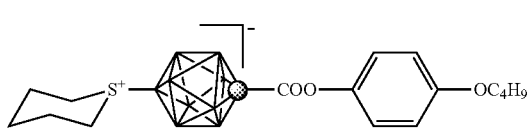

Compound IIB-b was synthesized from compound IIA-a and p-butoxyphenol using Method B of Example 17. Compound IIB-b was obtained at a 88% yield as an off-white solid after chromatography. Compound IIB-b was recrystallized twice from cold iso-octane/toluene (−20° C.) and twice from cold CH$_3$CN (−20° C.) giving pure compound IIB-b as white blades having an R$_f$=0.55 (CH$_2$Cl$_2$).

Example 21

Synthesis of the Ester Formed from [closo-1-CB$_9$H$_8$-1-COOH-10-(1-(4-C$_5$H$_{11}$)—C$_5$H$_9$S)] and 4-pentylphenol (Compound IIB-c)

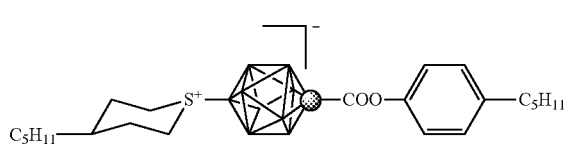

Compound IIB-c was synthesized from compound IIA-b and p-pentylphenol using Method B of Example 17. Compound IIB-c was obtained in 93% yield as an off-white solid after chromatography. The product was recrystallized twice from cold iso-octane/toluene (−20° C.) and three times from cold CH$_3$CN (−40° C.) giving compound IIBc as a white powder with an R$_f$=0.74 (CH$_2$Cl$_2$/hexane, 1:1).

Example 22

Synthesis of the Ester Formed from [closo-1-CB$_9$H$_5$-1-COOH-10-(1-(4-C$_5$H$_{11}$)—C$_5$H$_9$S)] and 4-butoxyphenol (Compound IIB-d)

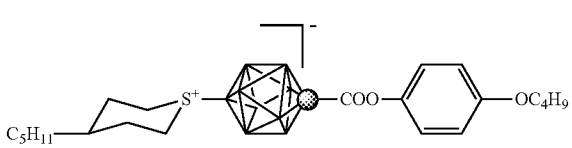

Compound IIB-d was synthesized from compound IIA-b and p-butoxyphenol using Method B of Example 17. Compound IIB-d was obtained in 86% yield as an off-white solid after chromatography. The product was recrystallized twice from cold iso-octane/toluene (−20° C.) and twice from cold CH$_3$CN (−40° C.) giving pure Compound IIB-d as white leaflets with an R$_f$=0.7 (CH$_2$Cl$_2$/hexane, 1:1).

Example 23

Synthesis of the Ester Formed from [closo-1-CB$_9$H$_5$-1-COOH-10-(1-(4-C$_3$H$_7$)—C$_5$H$_9$S)] and 4-butoxyphenol (Compound IIB-e)

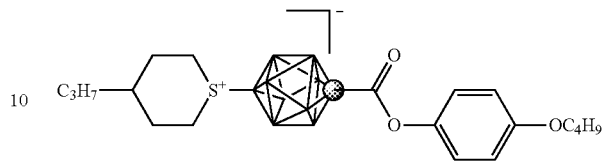

Compound IIB-e was synthesized from compound IIA-c and p-butoxyphenol using method B of Example 17. Compound IIB-e was obtained as an off-white solid after column chromatography (CH$_2$Cl$_2$/hexane, 1:1). It was recrystallized from iso-octane/toluene (−10° C.) and twice from cold MeOH (−10° C.) to give pure compound IIB-e as colorless microcrystals.

Example 24

Synthesis of the Ester Formed from [closo-1-CB$_9$H$_5$-1-COOH-10-(1-(4-C$_3$H$_7$)—C$_5$H$_9$S)] and 3,4,5-trifluorophenol (Compound IIB-f)

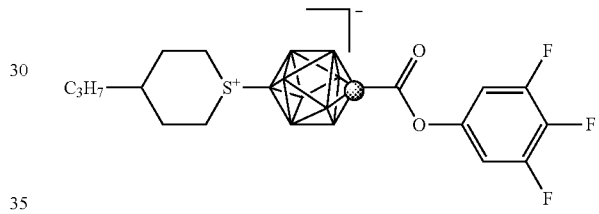

Compound IIB-f was synthesized from compound IIA-c and 3,4,5-trifluorophenol using method B of Example 17. Compound IIB-f was obtained in 56% yield as a white solid after column chromatography (CH$_2$Cl$_2$/hexane, 1:2). It was recrystallized from iso-octane/toluene (−10° C.) to give pure compound IIB-f as colorless microcrystals.

Example 25

Synthesis of [closo-1-CB$_9$H$_8$-1-NHBoc-10-I]$^-$NEt$_4^+$ (Compound 5•[NEt$_4$])

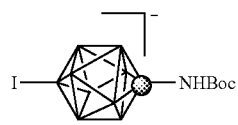

A suspension of acid [closo-1-CB$_9$H$_8$-1-COOH-10-I]$^-$NEt$_4^+$ (Compound 1•[NMe$_4$], 2.94 g, 7.02 mmol) in anhydrous CH$_2$Cl$_2$ (30 mL) was treated with neat (COCl)$_2$ (0.65 mL, 7.72 mmol). Vigorous bubbling of CO and CO$_2$ gases was observed followed by the dissolution of the substrate and the formation of a clear slight yellow solution. The solution was stirred for 1 hr at room temperature followed by filtration to remove insoluble particulates. The mother liquor was evaporated to dryness giving 3.10 g of crude [closo-1-CB$_9$H$_9$-1-COCl-10-I]$^-$NEt$_4^+$ as a white solid.

Crude [closo-1-CB$_9$H$_8$-1-COCl-10-I]$^-$NEt$_4^+$ (3.10 g, 7.02 mmol) was dissolved in anhydrous CH$_2$Cl$_2$ (10 mL) and added via syringe to solid anhydrous ZnCl$_2$ (0.096 g, 0.702 mmol) under N$_2$ atmosphere. The reaction mixture was cooled to 0° C., and Me₃SiN₃ (1.01 mL, 7.72 mmol) was added at once. The reaction mixture was stirred at 0° C. for an additional 30 min after which it was stirred for 4 hrs at rt. The reaction mixture was poured into ice-cold H₂O (50 mL) and extracted with CH₂Cl₂ (3×20 mL). The organic layers were combined, dried (MgSO₄), filtered, and solvent was removed in vacuo giving 3.09 g of crude [closo-1-CB₉H₈-1-CON₃-10-I]⁻NEt₄⁺ as a white crystalline solid. The crude product was contaminated with up to about 15% of [closo-1-CB₉H₈-1-COOH-10-I]⁻NEt₄⁺ (Compound 1•[NEt₄])

Crude [closo-1-CB₉H₈-1-CON₅-10-I]⁻NEt₄⁺ (3.09 g, 6.96 mmol) was dissolved in anhydrous CH₃CN (30 mL) and refluxed for 1 hr. The reaction was cooled to room temperature, solvent removed, and the residue was dried in vacuo giving 2.90 g of crude [closo-1-CB₉H₈-1-NCO-10-I]⁻NEt₄⁺ as a slight yellow solid.

A solution of anhydrous tert-butanol (3.33 mL, 34.85 mmol), anhydrous CH₃CN (30 mL), and crude [closo-1-CB₉H₈-1-NCO-10-I]⁻NEt₄⁺ (2.90 g, 6.97 mmol) was stirred at reflux for 2 hr after which solvents were removed leaving 3.06 g of crude compound 5•[NEt₄] as a yellow solid. The crude solid was dissolved in CH₂Cl₂ and passed through a silica gel plug first washed with 2% NEt₃ in CH₂Cl₂. Elution with a buffered CH₃CN/CH₂Cl₂ solution (2% NEt₃, 10% CH₃CN, 88% CH₂Cl₂) afforded 1.98 g (53% yield based on starting acid [closo-1-CB₉H₈-1-COOH-10-I]⁻NEt₄⁺) of pure compound 5•[NEt₄] as a slight yellow solid. A small portion of the product was recrystallized from aqueous EtOH for analysis: mp 156-158° C. Further elution gave 0.75 g of a 90:10 mixture of compound 5•[NEt₄] and compound 1•[NEt₄].

Example 26

Synthesis of [closo-1-CB₉H₈-1-N₂-10-I] (Compound 7)

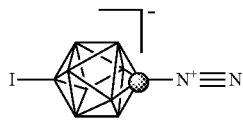

A suspension of Compound 5•[NEt₄] (1.18 g, 2.41 mmol) in a 1:3 mixture of conc. HCl and CH₃OH (50 mL) was heated gently until all solids dissolved, and stirring was continued at room temperature for 18 hrs. H₂O (20 mL) was added and CH₃OH was removed in vacuo. Conc. HCl (3 mL) was added, and the resulting solution was extracted with Et₂O (3×30 mL). The organic layers were combined, dried (Na₂SO₄), and solvents evaporated in vacuo to give 0.604 g of crude compound 6 as a transparent film, which slowly solidified as a light brown glass.

The crude compound 6 was dissolved in a 1:1 mixture of AcOH/H₂O (6 mL), and an aqueous solution of NaNO₂ (0.183 g, 2.65 mmol) in H₂O (4 mL) was added dropwise (~1 drop/sec) at 0° C. Immediately, a white precipitate began to form. The reaction temperature was maintained for 30 min, H₂O (2 mL) was added, and the precipitate was filtered and dried to give 0.577 g (88% yield) of compound 7 as a white crystalline solid having a melting point of 106° C. dec.

Example 27

Synthesis of [closo-1-CB₉H₈-1-SCHN(Me)₂-10-I] (Compound 8)

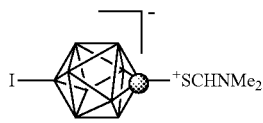

A yellow solution of compound 7 (0.200 g, 0.74 mmol) and freshly distilled Me₂NCHS (3.0 mL) was stirred at room temperature for 6 hr. Excess Me₂NCHS was removed by vacuum distillation (80° C., 0.25 mm Hg) leaving 0.296 g of crude product as a slight yellow oil that slowly crystallized. The crude product was washed with toluene until the decant was no longer yellow giving 0.245 g (100% yield) of crude compound 8 as yellowish solid.

Example 28

Synthesis of [closo-1-CB₉H₈-1-NH₂-10-C₆H₁₃]⁻ NMe₄⁺ (Compound 9a•[NMe₄])

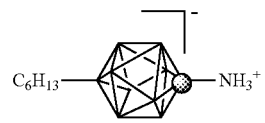

To a three-necked flask under inert atmosphere attached with reflux condenser, a glass stopcock, and septum containing iodo amine [closo-1-CB₉H₈-1-NH₂-10-I]⁻NHMe₃⁺ (Compound 6•[NHMe₃], 0.635 g, 1.98 mmol) dissolved in anhydrous THF (20 mL) was added C₆H₁₃MgBr (9.9 mL, 19.8 mmol, 2.0 M). A bubbler was attached, and the reaction mixture was heated at reflux for 30 min. (PPh₃)₂PdCl₂ (0.186 g, 0.26 mmol) and CuI (0.075 g, 0.393 mmol) were added, and the reaction was stirred at reflux, and reaction progress was monitored by ¹¹B NMR at 24 hr intervals. If the reaction was incomplete, additional equivalents of C₆H₁₃MgBr, (PPh₃)₂PdCl₂, and CuI were added and heating continued. A 5% HCl solution (200 mL) was added, and the reaction mixture was extracted with Et₂O (3×50 mL). The organic layers were combined, dried (Na₂SO₄), filtered, and evaporated giving 1.60 g of an oily brown residue. The residue was purified by column chromatography (CH₃CN/CH₂Cl₂, 1:4) giving 0.140 g of crude acid extract [closo-1-CB₉H₈-1-NH₂-10-C₆H₁₃]⁻H₃O⁺. Water (5 mL) and NMe₄⁺OH⁻.5H₂O (0.109 g, 0.60 mmol) were added producing a milky suspension. The product was extracted with CH₂Cl₂. Solvents were removed to dryness in vacuo giving 0.190 g (33% yield) of compound 9a•[NMe₄] as a colorless film that slowly crystallized.

Example 29

General Procedure for the Synthesis of Class IIIA Compounds (R'=I)

A yellow solution of crude compound 8 (about 1 molar equivalent), NMe₄⁺OH⁻.5H₂O (about 1 molar equivalent), and an appropriate 3-substituted 1,5-dibromopentane RCH(CH₂CH₂Br)₂ (about 1 molar equivalent) in anhydrous CH₃CN may be stirred at room temperature for 12 hr. The reaction mixture may be filtered and evaporated to dryness. The resulting residue may be washed with hexane giving crude product, which may be passed through a short silica gel column (CH₂Cl₂/hexane, 1:1) giving [closo-1-CB₉H₈-1-(4-R—C₅H₉S)-10-I]⁻ (Class IIIA compounds) as the fast-moving component. Further purification may be accomplished by recrystallization (toluene/iso-octane mixture).

Example 30

Synthesis of [closo-1-CB₉H₈-1-(4-C₅H₁₁C₅H₉S)-10-I] (Compound IIIA-a)

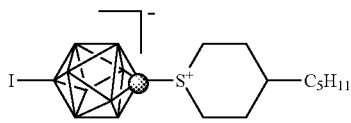

Compound IIIA-a was synthesized from compound 8 and 1,5-dibromo-3-pentylpentane in 39% yield as a white solid. It was recrystallized from iso-octane/toluene (−20° C.) to give pure compound IIIA-a as colorless microcrystals.

Example 31

Synthesis of [closo-1-CB$_9$H$_8$-1-(4-C$_3$H$_7$C$_6$H$_4$CH$_2$CH$_2$C$_5$H$_9$S)-10-I] (Compound IIIA-b)

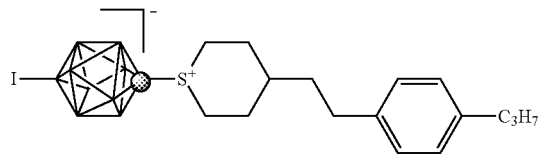

Compound IIIA-b was synthesized from compound 8 and 1,5-dibromo-3-(2-(4-propylphenyl)ethyl)pentane in 45% yield as a white solid. It was recrystallized from iso-octane/toluene (−20° C.) to give pure compound IIIA-b as colorless microcrystals.

Example 32

[closo-1-CB$_9$H$_8$-1-(4-C$_5$H$_{11}$C$_6$H$_{10}$CH$_2$CH$_2$C$_5$H$_9$S)-10-I] (Compound IIIA-c)

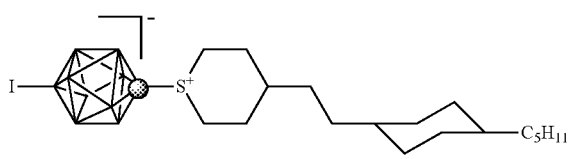

Compound IIIA-c was synthesized from compound 8 and 1,5-dibromo-3-(2-(4-trans-pentylcyclohexyl)ethyl)pentane in 43% yield as a white solid. It was recrystallized from iso-octane/toluene (−20° C.) to give pure ester IIIA-c as colorless microcrystals.

Example 33

General Procedure for Preparation of Class IIIB Compounds (R'≠Halogen)

To a three-necked flask under inert atmosphere attached with reflux condenser, a glass stopcock, and septum containing Pd$_2$ dba$_3$ and [HPCy$_3$]BF$_4$ may be added an anhydrous NMP/THF mixture. A solution of R'ZnCl prepared from R'MgBr and anhydrous ZnCl$_2$ may be added resulting in the formation of a yellow/orange suspension that slowly turns green. A Class IIIA compound may be dissolved in anhydrous THF via syringe, the septum may be replaced with a glass stopcock, and the reaction may be stirred at 85° C. Reaction progress may be monitored at 24 hr intervals by $^{11}$B NMR analysis. If the reaction is incomplete, additional equivalents of Pd$_2$ dba$_3$, [HPCy$_3$]BF$_4$, and C$_6$H$_{13}$ZnCl may be added and stirring continued at 85° C. After about 72 hr, the reaction may be quenched with a saturated solution of NH$_4$Cl, extracted into Et$_2$O, dried (Na$_2$SO$_4$) and evaporated. NMP may be removed via vacuum distillation (0.5 mm Hg, 50° C.) giving crude product, which may be purified via column chromatography (CH$_2$Cl$_2$/hexane).

Example 34

Synthesis of [closo-1-CB$_9$H$_8$-1-(4-C$_5$H$_{11}$C$_5$H$_9$S)-10-C$_6$H$_{13}$] (Compound IIIB-a)

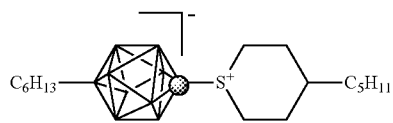

Using the method of Example 31, Compound IIIB-a was obtained in 58% yield as a yellowish solid, which was purified further by washing with hot hexane and recrystallization (toluene/iso-octane mixture).

Example 35

[closo-1-CB$_9$H$_8$-1-(4-C$_3$H$_7$C$_6$H$_4$CH$_2$CH$_2$C$_5$H$_9$S)-10-C$_5$H$_{11}$] (Compound IIIB-b)

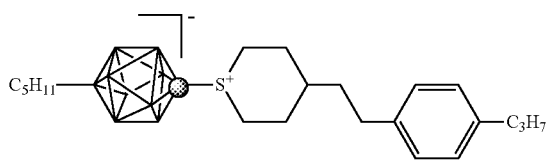

Compound IIIB-b was purified using the method of Example 31.

Example 36

[closo-1-CB$_9$H$_8$-1-(4-C$_5$H$_{11}$C$_6$H$_{10}$CH$_2$CH$_2$C$_5$H$_9$S)-10-C$_3$H$_7$] (Compound IIIB-c)

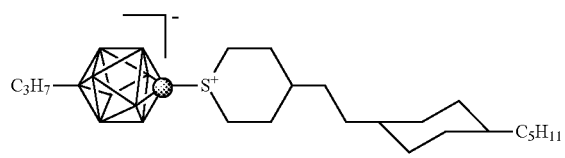

Compound IIIB-c was purified using the method of Example 31.

Example 37

Transition Temperatures for the Class I-III Compounds

The Class I-III compounds were analyzed using polarizing optical microscopy (POM) and differential scanning calorimetry (DSC). Tables 1-4 below show the transition temperatures for various Class I-III compounds. Some compounds have nematic phases (e.g., enantiotropic or monotropic nematic phases), whereas other compounds do not. If a compound has a nematic phase, then it structurally may be highly compatible for use as an additive in mixtures with nematic hosts. However, even if a compound does not have a nematic phase, it still may be very useful as an additive.

As shown in Table I below, three of the Class I compounds (compounds IB-b, IB-c and IB-e) exhibited enantiotropic nematic phases, and two (compounds IB-d and IB-f) exhibited monotropic nematic phases.

TABLE 1

Transition temperatures (° C.) for Class IB compounds.

| Compound | R | R' | Crystal | | Nematic | | Isotropic |
|---|---|---|---|---|---|---|---|
| IB-a | H | cyclohexyl | • | 175 | | | • |
| IB-b | $C_7H_{15}O$ | bicyclo-$C_5H_{11}$ | • | 161 | • | 231 | • |
| IB-c | $C_7H_{15}O$ | cyclohexyl-$C_5H_{11}$ | • | 148 | • | 161 | • |
| IB-d | $C_7H_{15}O$ | phenyl-$C_5H_{11}$ | • | 120 | (• | 114) | • |
| IB-e | $C_7H_{15}O$ | phenyl-$OC_4H_9$ | • | 122 | • | 156 | • |
| IB-f | $C_7H_{15}O$ | phenyl-$CN$ | • | 128 | (• | 129) | • |

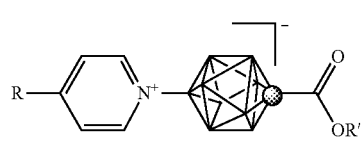

In contrast, none of the Class II compounds exhibited enantiotropic nematic phases, while two (compounds IIB-d and IIB-e) exhibited monotropic nematic phases, as shown in Table 2 below. Moreover, the melting points for the Class II compounds generally were lower than for the Class I compounds.

TABLE 2

Transition temperatures (° C.) for Class IIB compounds.

| Compound | R | R' | Crystal | | Nematic | | Isotropic |
|---|---|---|---|---|---|---|---|
| IIB-a | H | phenyl-$OMe$ | • | 158 | | | • |
| IIB-b | H | phenyl-$OC_4H_9$ | • | 138.5 | | | • |
| IIB-c | $C_5H_{11}$ | phenyl-$C_5H_{11}$ | • | 97 | | | • |
| IIB-d | $C_5H_{11}$ | phenyl-$OC_4H_9$ | • | 101 | (• | 97) | • |
| IIB-e | $C_3H_7$ | phenyl-$OC_4H_9$ | • | 111 | (• | 96) | • |

TABLE 2-continued

Transition temperatures (° C.) for Class IIB compounds.

| Compound | R | R' | Crystal | Nematic | Isotropic |
|---|---|---|---|---|---|
| IIB-f | C₃H₇ | (2,3,4-trifluorophenyl) | • | 139 | • |

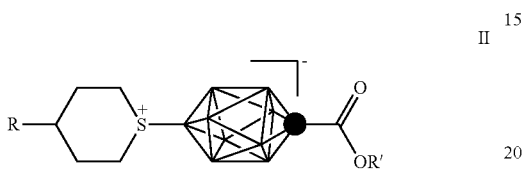

II

As shown in Tables 3 and 4 below, the Class III compounds have significantly higher melting points than compounds of Class I and Class II due to the higher molecular dipole moment of the Class III zwitterionic core than the Class I and II zwitterionic cores.

TABLE 3

Transition temperatures (° C.) for Class IIIA compounds.

| Compound | R | R' | Crystal | Nematic | Isotropic |
|---|---|---|---|---|---|
| IIIA-a | C₅H₁₁ | I | • | 230 | • |
| IIIA-b | (phenyl-C₃H₇) | I | • | 241 | • |
| IIIA-c | (cyclohexyl-C₅H₁₁) | I | • | 214 | • |

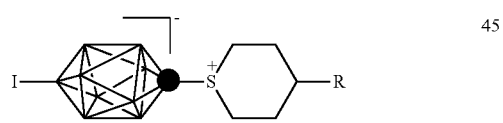

TABLE 4

Transition temperatures (° C.) for Class IIIB compounds.

| Compound | R | R' | Crystal | Nematic | Isotropic |
|---|---|---|---|---|---|
| IIIB-a | C₅H₁₁ | C₆H₁₃ | • | 209 | • |
| IIIB-b | (phenyl-C₃H₇) | C₅H₁₁ | • | 198 | • |
| IIIB-c | (cyclohexyl-C₅H₁₁) | C₆H₁₃ | • | 255 | • |

Example 38

Preparation of Binary Mixtures with the Class I-III Compounds

The Class I-III compounds were investigated as low concentration additives to three nematic hosts: ClEster, 6-CHBT, and ZLI-1132. In the absence of additives, ClEster has a small negative $\Delta \in$, whereas 6-CHBT and ZLI-1132 have significant positive $\Delta \in$ (+7.6 for 6-CHBT and +11.5 for ZLI-1132) and are models for industrial LCD materials. Mixtures of the Class I-III compounds in the hosts ClEster, 6-CHBT or ZLI-1132 (~10 mg) were prepared in an open vial with agitation using a closed-end capillary tube with moderate heating supplied by a heat gun. The binary mixtures were analyzed by polarized optical microscopy (POM) to ensure that the mixtures were homogeneous. The mixtures were then allowed to condition for 3 hr at room temperature. The clearing temperature of each homogeneous mixture was determined by DSC differential scanning calorimetry as the peak of the transition.

Compounds IB-d, IB-f, IIB-c and IIIB-a were tested in various nematic hosts, as shown in Table 5 below. While compounds IB-d, IIB-c and IIIB-a all showed good solubility in ClEster to at least 15 mol %, compound IB-f only made a stable solution in ClEster at or below 3 mol %, and a 5.6 mol % solution was inhomogeneous after 4 hr at room temperature. Despite good solubility in ClEster, the pyridinium compound IB-d did not form homogenous solutions with 6-CHBT at a concentration even as low as 2.5 mol %. In contrast, the sulfonium compounds IIB-c and IIB-d both were soluble in ClEster and 6-CHBT hosts at concentrations up to about 11 mol %, which was the highest concentration tested. In addition, the sulfonium compound IIB-c formed a stable 2.8 mol % solution in ZLI-1132.

Of the Class I-III compounds, Class III compounds generally have the lowest solubility in nematic hosts, Class I compounds are the next most soluble, and Class II compounds are the most soluble. This trend is due to the higher molecular dipole moment of the Class III zwitterionic core than the Class I and II zwitterionic cores. The low solubility of Class IIIA compounds in nematic hosts may be increased by using substituting the iodine at B10 with an alkyl at that position as in the Class IIIB compounds. Further increases of solubility may be achieved by using substituted or unsubstituted alkyl chains, alkenyl chains, alkynyl chains, cyclohexyl rings, or other such substituents, such as for the R and R' substituents used in compound IIIB-c.

Example 39

Electrooptical Measurements of Binary Mixtures Containing Class I-III Compounds

Dielectric properties of solutions of selected Class I-III compounds in ClEster, 6-CHBT and/or ZLI-1132 were measured by a Liquid Crystal Analytical System (LCAS—Series II, LC Analytical Inc.) using GLCAS software version 0.951, which implements literature procedures for dielectric constants. The homogeneous binary mixtures were loaded into ITO electro-optical cells by capillary forces with moderate heating supplied by a heat gun. The cells (about 4 µm thick, electrode area of 0.581 cm$^2$ and anti-parallel rubbed polyimide layer 2°-3° pretilt) were obtained from LCA Inc., and their precise thickness (±0.05 m) was measured by LCAS using the capacitance method before the cells were filled. The filled cells were heated to an isotropic phase and were cooled to ambient temperature (23° C.) before measuring the dielectric properties. Default parameters were used for measurements: triangular shaped voltage bias ranging from 0.1-15 V for 3 and 4 and 0.1-30 V for 11 at 1 kHz frequency. The threshold voltage V$_{th}$ was measured at a 5% change. For each mixture, the measurement was repeated seven times for two cells. The first two measurements for each cell were discarded as conditioning measurements, and the remaining ten results were averaged to calculate the mixture's parameters. Dielectric parameters of pure hosts 6-CHBT and ZLI-1132 were obtained using the same protocol. For consistency, dielectric parameters for ClEster were obtained by averaging values obtained by extrapolation from a series of measurements for each additive. The averaged extrapolated values for the binary mixtures are higher than those measured in a set of homeotropic cells by about 0.2 for $\in_{\parallel}$ and $\in_{\perp}$ and lower by 0.03 for $\Delta \in$.

TABLE 5

Extrapolated thermal and dielectric parameters for selected binary mixtures in hosts.

| Compound | Host | $[T_{NI}]/°$ C. | $\in \parallel$ | $\in \perp$ | $\Delta \in$ |
|---|---|---|---|---|---|
| IB-d | ClEster | 103 ± 1 | 54.8 ± 0.3 | 12.8 ± 0.1 | 42.0 ± 0.3 |
| IB-f | ClEster | 95.5 ± 1 | 136.2 ± 0.3 | 22.8 ± 0.3 | 113.4 ± 0.6 |
| IIB-c | ClEster | 89 ± 2 | 35.0 ± 0.2 | 9.7 ± 0.2 | 25.3 ± 0.2 |
| IIB-c | 6-CHBT | 112 ± 2 | 41.3 ± 0.2 | 11.8 ± 0.2 | 29.5 ± 0.3 |
| IIB-c | ZLI-1132 | 36 | 30.7 | 8.6 | 22.1 |
| IIB-d | 6-CHBT | 133 ± 2 | 47.7 ± 0.1 | 12.2 ± 0.1 | 35.5 ± 0.1 |
| IIIB-a | ClEster | 92 | 84 ± 1 | 23 ± 1 | 61 ± 2 |

Figure 8:
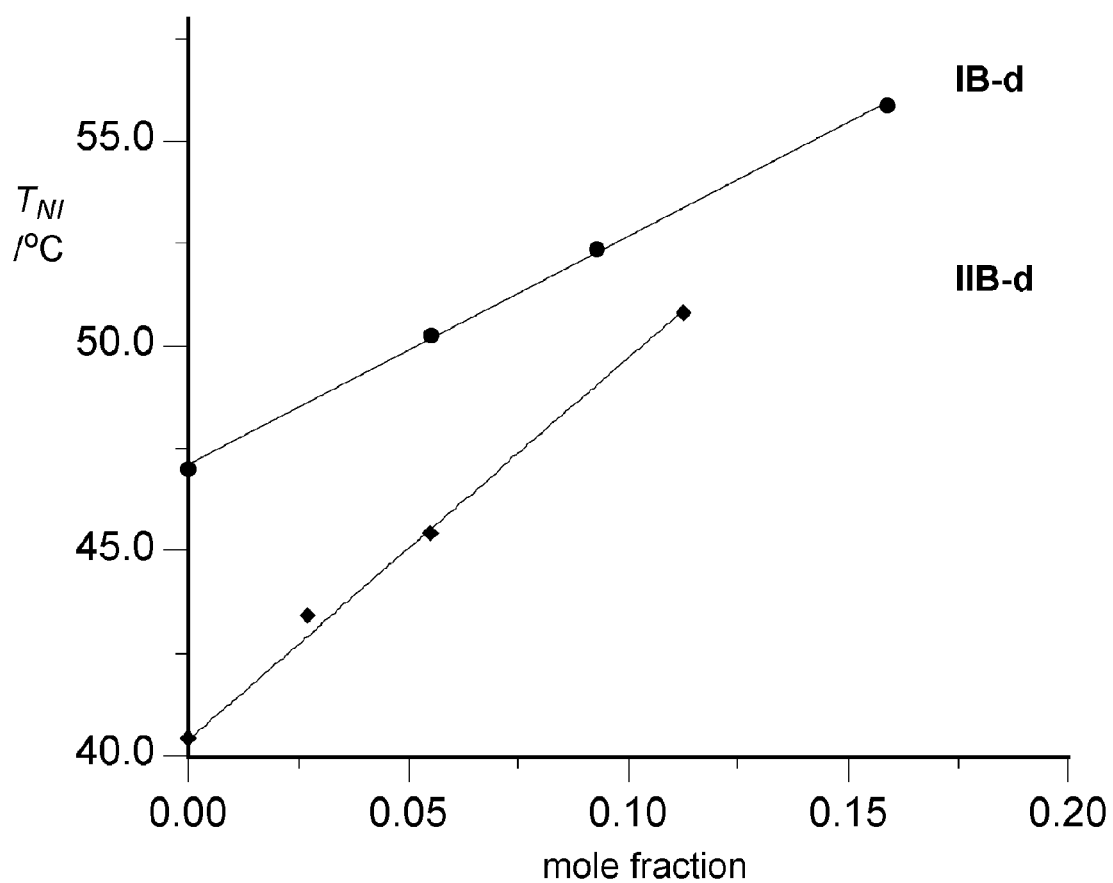
FIG. 8 is a graph comparing a plot of the transition temperature between the nematic and isotropic phases of a binary mixture of a Class IB compound in ClEster as a function of the concentration of the Class IB compound, to a plot of the transition temperature between the nematic and isotropic phases of a binary mixture of a Class IIB compound in 6-CHBT as a function of the concentration of the Class IIB, according to aspects of the present disclosure.

Many of the compounds described herein exhibit ideal miscibility with nematic hosts at low concentrations. FIG. 8 is a graph comparing a plot of the transition temperature (T$_{NI}$) between the nematic and isotropic phases of a binary mixture of compound IB-d in ClEster as a function of the concentration of the compound IB-d, to a plot of the transition temperature between the nematic and isotropic phases of a binary mixture of a compound IIB-d in 6-CHBT as a function of the concentration of the compound IIB-d. Plots such as the ones shown in FIG. 8 were used to extrapolate the nematic-isotropic transition temperatures (so called virtual isotropic transition temperatures) for pure additive (i.e., mole fraction=1), which are shown in Table 5. These extrapolated T$_{NI}$ values are favorably high, showing that these compounds may be used as suitable additives for mixtures with nematic hosts. Notably, the binary mixtures made with all the Class I-III compounds demonstrate that Class I-III compounds are compatible as additives to a variety of nematic hosts. Even the non-liquid crystalline compound IIIB-a behaves in ClEster solutions as if it were a nematic liquid with an extrapolated T$_{NI}$ of about 92° C., while the pure Compound IIIB-a actually melts at 209° C.

Figure 9:
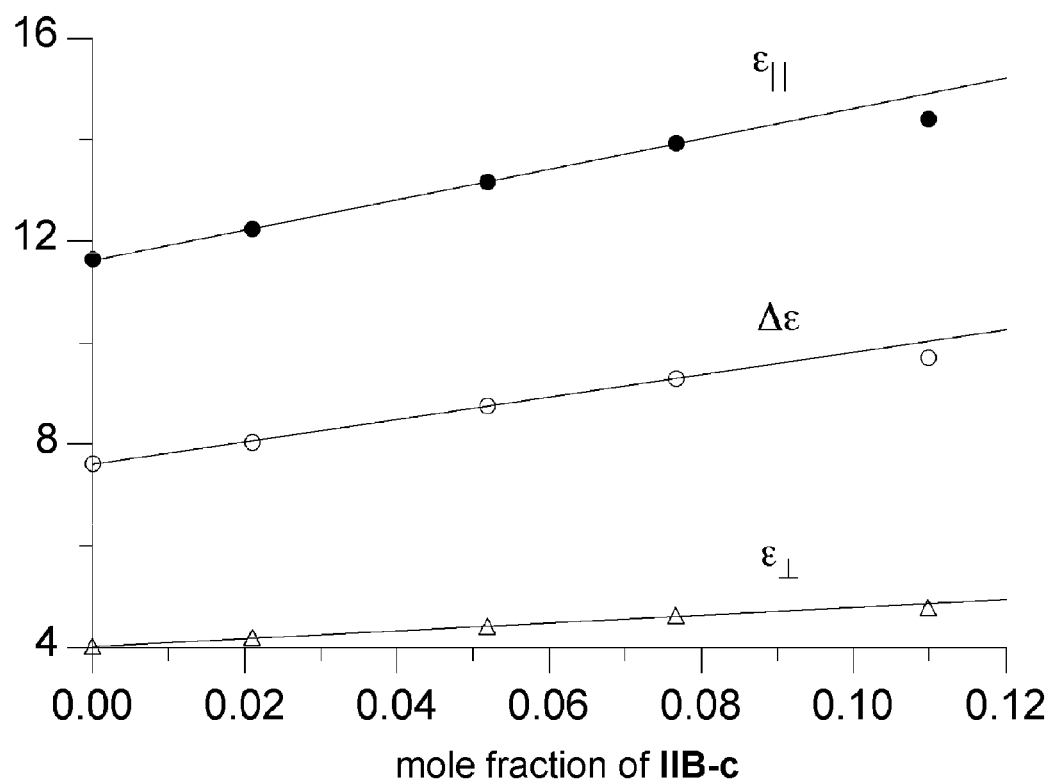
FIG. 9 is a plot of the dielectric parameters of a binary mixture of a Class IIB compound in 6-CHBT as a function of the concentration of the Class IIB compound, according to aspects of the present disclosure.

Class I and II compounds were observed to exhibit linear dependence of the dielectric parameters of the binary mixtures on the concentration of the additive. This is illustrated in FIG. 9, which is a plot of the dielectric parameters for compound IIB-c in the nematic host 6-CHBT as a function of the concentration of compound IIB-c. Plots such as the ones shown in FIG. 9 were used to extrapolate the dielectric parameters for pure additive (mole fraction=1) for Class I and II compounds. Compound IIIB-a was observed to exhibit non-linear dependence of the dielectric parameters of the binary mixture with ClEster on the concentration of the additive. The extrapolated values for the dielectric parameters for pure compound IIIB-a were obtained using a curve fitting analysis of the data to infinite dilutions of compound IIIB-A. The extrapolated values for $\in_{\parallel}$, $\in_{\perp}$ and $\Delta \in$ are shown in Table 5, and demonstrate that Class I-III compounds, when used as additives in nematic hosts, effect significant increases in the dielectric anisotropy of the nematic hosts.

Of the Class I-III compounds, the Class III compounds appear to be most effective at effecting large changes in the dielectric anisotropy of nematic hosts, the Class I compounds are the next most effective, and the Class II compounds are the least effective. This trend follows the same trend as the molecular dipole moments of the key zwitterionic fragments in each of Classes I-III. Moreover, when these fundamental zwitterionic fragments are combined with an additional dipolar functional group (such as the —CN in compound IBM, unusually large dielectric anisotropies result.

Example 40

LCDs

Compounds and binary mixtures of the present disclosure (e.g., those set forth in the preceding examples) are incorporated into LCDs using methods known in the art.

REFERENCES

In addition to any reference identified throughout the present disclosure, the following references are herein incorporated by reference in their entireties for all purposes:

Fréedericksz and Zolina, *Trans. Faraday Soc.* 1933, 29, 919-930.
Wu, S. T.; Coates, D.; Bartmann, E. *Liq. Cryst.* 1991, 10(5), 635-646.
Rague Schleyer, P. V.; Najafian, K. *Inorg. Chem.* 1998, 37, 3454-3470.
Pakhomov, S; Kaszynski, P. *Inorg. Chemistry,* 2000, 39, 2243-2245.
Brellochs, B.; et al. "New Routes to Carboranes," *Contemporary Boron Chemistry* 2000, 212-214.
Franken, A.; et al. *Collection of Czechoslovak Chemical Communications* 2002, 67, 869-912.
Franken, A.; et al. *Dalton Trans.* 2004, 3552-3561.
Ringstrand, B.; Monobe, H.; Kaszynski, P. *J. Mater. Chem.* 2009, 19, 4805-4812.
Ringstrand, B.; Kaszynski, P.; Januszko, A.; Young, V. G., Jr. *J. Mater. Chem.* 2009, 19, 9204-9212.
Ringstrand, B.; Kaszynski, P.; Franken, A. *Inorg. Chem.* 2009, 48, 7313-7329.
Ringstrand, B.; Kaszynski, P.; Young, V. G., Jr.; Janousek, Z. *Inorg. Chem.* 2010, 49, 1166-1179.
Ringstrand, B.; Kaszynski, P. *J. Mater. Chem.* 2010, 20, 9613-9615.
Ringstrand, B.; Kaszynski, P. *J. Mater. Chem.* 2010, DOI: 10.1039/C0JM2075C.

What is claimed is:

1. A compound comprising the following structure:

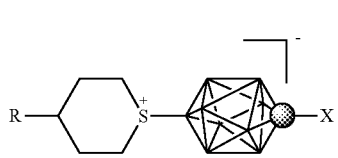

wherein

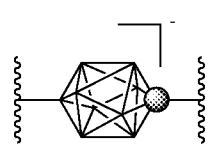

is a caged boron structure where the sphere of the caged boron structure is C and each non-sphere vertex of the caged boron structure is B—H;

wherein R is H, an alkyl, a cycloalkyl, a bicycloalkyl, an alkenyl, a cycloalkenyl, a bicycloalkenyl, an alkynyl, an acyl, an aryl, an alkylaryl, a halogen, a cyano group, or an isothiocyanoto group, or where R is a group that forms an ether, a ketone, an ester, a thioester, a sulfide, or a sulfone;

wherein X is COOR' or COSR'; and wherein R' is H, an alkyl, a cycloalkyl, a bicycloalkyl, an alkenyl, a cycloalkenyl, a bicycloalkenyl, an alkynyl, or an aryl.

2. The compound of claim 1, wherein R is H, a $C_2$-$C_9$ alkyl, a $C_2$-$C_9$ alkenyl, or a $C_2$-$C_9$ alkoxy.

3. The compound of claim 1, wherein R is propyl or heptyl.

4. The compound of claim 1, wherein X is COOR'.

5. The compound of claim 1, wherein R' is H, a $C_2$-$C_9$ alkyl, a $C_2$-$C_9$ alkenyl, a $C_6$-$C_8$ cycloalkyl, or an aryl.

6. The compound of claim 1, wherein R' is

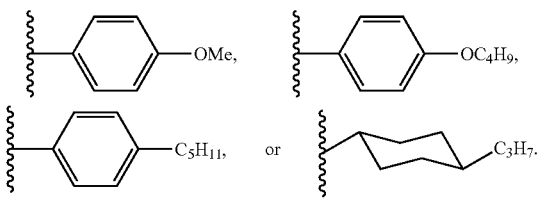

7. The compound of claim 1, wherein the compound is:

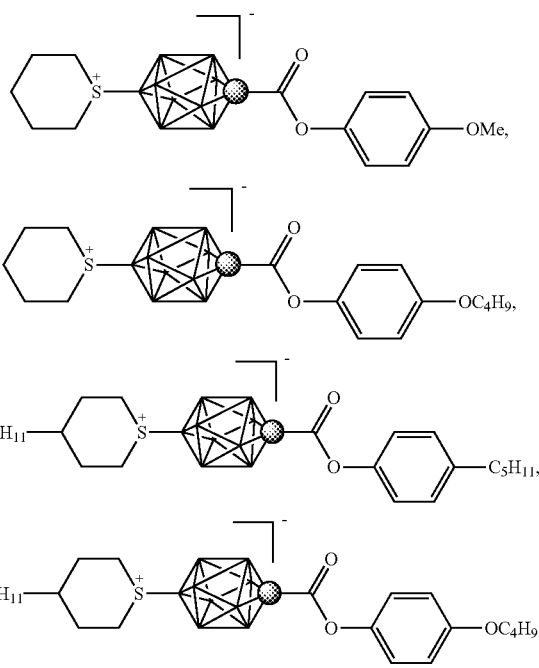

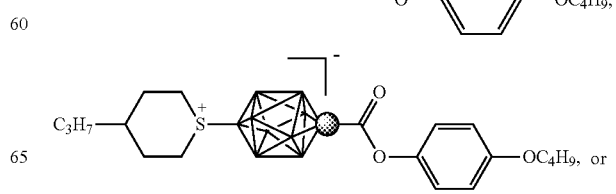

-continued

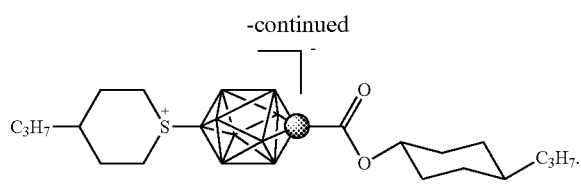

8. A method of making the compound of claim 1, comprising:
heating a mixture comprising

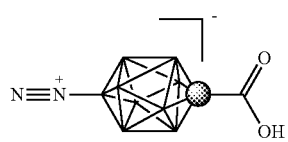

and a thiocarbonyl to form an intermediate; and
reacting the intermediate under hydrolytic conditions with RCH(CH$_2$CH$_2$X')$_2$, where X' is a halogen.

9. A method of making the compound of claim 1, comprising heating a mixture comprising

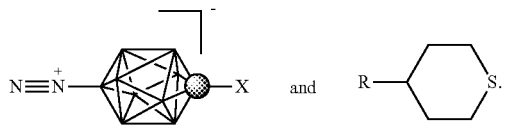

10. A mixture comprising the compound of claim 1 and a nematic host.

11. A liquid crystal display comprising the compound of claim 1.

12. A television set, a laptop computer, a computer monitor, a hand-held communication device, a gaming device, a watch, a cash register, a clock, or a calculator comprising the liquid crystal display of claim 11.

* * * * *